United States Patent [19]

Leschinsky et al.

[11] Patent Number: 5,728,122
[45] Date of Patent: Mar. 17, 1998

[54] GUIDE WIRE WITH RELEASEABLE BARB ANCHOR

[75] Inventors: Boris Leschinsky, Waldwick; Jeffrey Urbanski, Sparta; Mark Follman, Glen Rock, all of N.J.

[73] Assignee: Datascope Investment Corp., Montvale, N.J.

[21] Appl. No.: 484,911

[22] Filed: Jun. 7, 1995

Related U.S. Application Data

[63] Continuation-in-part of Ser. No. 182,501, Jan. 18, 1994, abandoned.

[51] Int. Cl.$^6$ ...................................................... A61B 17/08
[52] U.S. Cl. ........................... 606/213; 606/217; 128/772; 604/96; 604/282
[58] Field of Search ............................... 128/772; 606/213, 606/215, 217, 222, 223, 224, 225, 226, 227, 228, 229, 232, 233; 604/164, 282, 96

[56] References Cited

U.S. PATENT DOCUMENTS

| | | |
|---|---|---|
| Re. 34,866 | 2/1995 | Kensey et al. . |
| 2,898,913 | 8/1959 | Ritter et al. . |
| 3,447,533 | 6/1969 | Spicer . |
| 3,572,335 | 3/1971 | Robinson . |
| 4,007,743 | 2/1977 | Blake . |
| 4,578,061 | 3/1986 | Lemelson . |
| 4,588,395 | 5/1986 | Lemelson . |
| 4,619,261 | 10/1986 | Guerriero . |
| 4,638,803 | 1/1987 | Rand . |
| 4,744,364 | 5/1988 | Kensey . |
| 4,790,819 | 12/1988 | Li et al. . |
| 4,832,688 | 5/1989 | Sagae et al. . |
| 4,838,280 | 6/1989 | Haaga . |
| 4,852,568 | 8/1989 | Kensey . |
| 4,878,906 | 11/1989 | Lindemann et al. . |
| 4,895,564 | 1/1990 | Farrell . |
| 4,900,303 | 2/1990 | Lemelson . |
| 4,929,246 | 5/1990 | Sinofosky . |
| 4,941,874 | 7/1990 | Sandow et al. . |
| 5,021,059 | 6/1991 | Kensey .................... 606/232 X |
| 5,041,129 | 8/1991 | Hayhurst et al. ................. 606/232 |
| 5,053,046 | 10/1991 | Janese . |
| 5,061,274 | 10/1991 | Kensey . |
| 5,074,840 | 12/1991 | Yoon . |
| 5,108,421 | 4/1992 | Fowler . |
| 5,123,914 | 6/1992 | Cope .................................. 606/232 |
| 5,129,882 | 7/1992 | Weldon et al. . |
| 5,192,300 | 3/1993 | Fowler . |
| 5,192,302 | 3/1993 | Kensey et al. . |
| 5,221,259 | 6/1993 | Weldon et al. . |
| 5,222,974 | 6/1993 | Kensey et al. . |
| 5,275,616 | 1/1994 | Fowler . |
| 5,282,827 | 2/1994 | Kensey et al. . |
| 5,290,310 | 3/1994 | Makower et al. . |
| 5,292,332 | 3/1994 | Lee .................................. 606/213 |

(List continued on next page.)

FOREIGN PATENT DOCUMENTS

| | | |
|---|---|---|
| 0476178A1 | 3/1992 | European Pat. Off. . |
| 2641692 | 7/1990 | France . |
| 8907370.3 | 9/1989 | Germany . |
| 782814 | 11/1990 | U.S.S.R. . |
| 1509023 | 4/1978 | United Kingdom . |
| 89-11301 | 11/1989 | WIPO . |
| 91/16858 | 11/1991 | WIPO . |
| 92/22252 | 12/1992 | WIPO . |
| 93/08740 | 5/1993 | WIPO . |
| 93/08746 | 5/1993 | WIPO . |
| 93/10714 | 6/1993 | WIPO . |
| 94/17738 | 8/1994 | WIPO . |
| 94/28800 | 12/1994 | WIPO . |

*Primary Examiner*—Sam Rimell
*Attorney, Agent, or Firm*—Lerner, David, Littenberg, Krumholz & Mentlik

[57] ABSTRACT

An insertion guide wire with an anchor formed in the distal end for precisely locating a subcutaneous arterial wound and guiding a plug of hemostatic material thereto. When the hemostatic material is properly placed, the anchor can be released and the guide wire removed, leaving no foreign object in the lumen of the artery.

44 Claims, 18 Drawing Sheets

U.S. PATENT DOCUMENTS

| | | |
|---|---|---|
| 5,304,117 | 4/1994 | Wilk . |
| 5,310,407 | 5/1994 | Casale . |
| 5,312,435 | 5/1994 | Nash et al. . |
| 5,320,639 | 6/1994 | Rudnick . |
| 5,326,350 | 7/1994 | Li . |
| 5,330,446 | 7/1994 | Weldon et al. . |
| 5,342,393 | 8/1994 | Stack . |
| 5,350,399 | 9/1994 | Erlebacher et al. . |
| 5,370,660 | 12/1994 | Weinstein et al. . |
| 5,388,588 | 2/1995 | Nabai et al. . |
| 5,391,183 | 2/1995 | Janzen et al. . |
| 5,403,278 | 4/1995 | Ernst et al. . |
| 5,411,520 | 5/1995 | Nash et al. . |
| 5,419,765 | 5/1995 | Weldon et al. . |
| 5,431,639 | 7/1995 | Shaw . |
| 5,441,517 | 8/1995 | Kensey et al. . |
| 5,443,481 | 8/1995 | Lee . |
| 5,451,235 | 9/1995 | Lock et al. . |
| 5,454,833 | 10/1995 | Boussignac et al. . |
| 5,486,195 | 1/1996 | Myers et al. . |

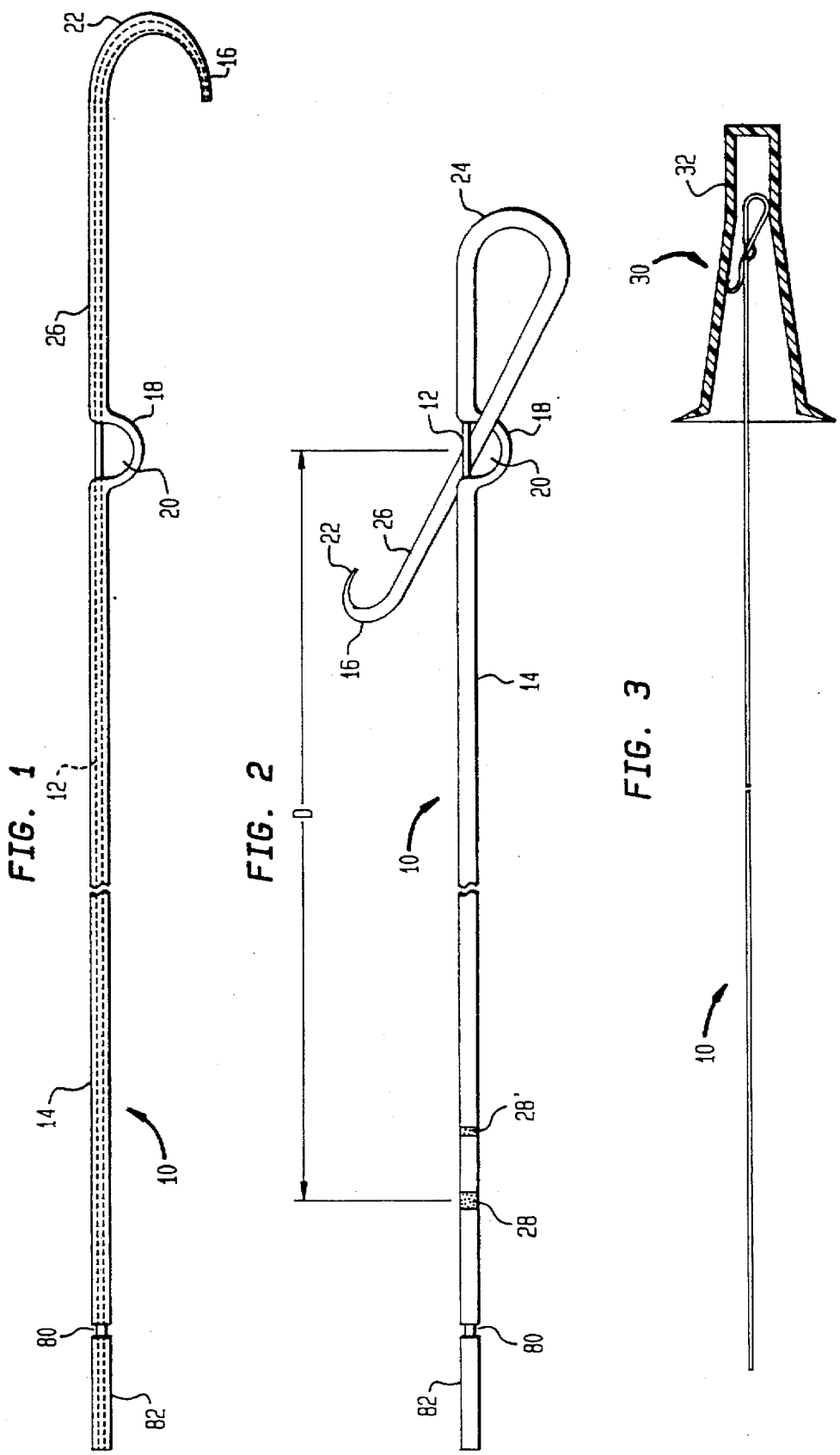

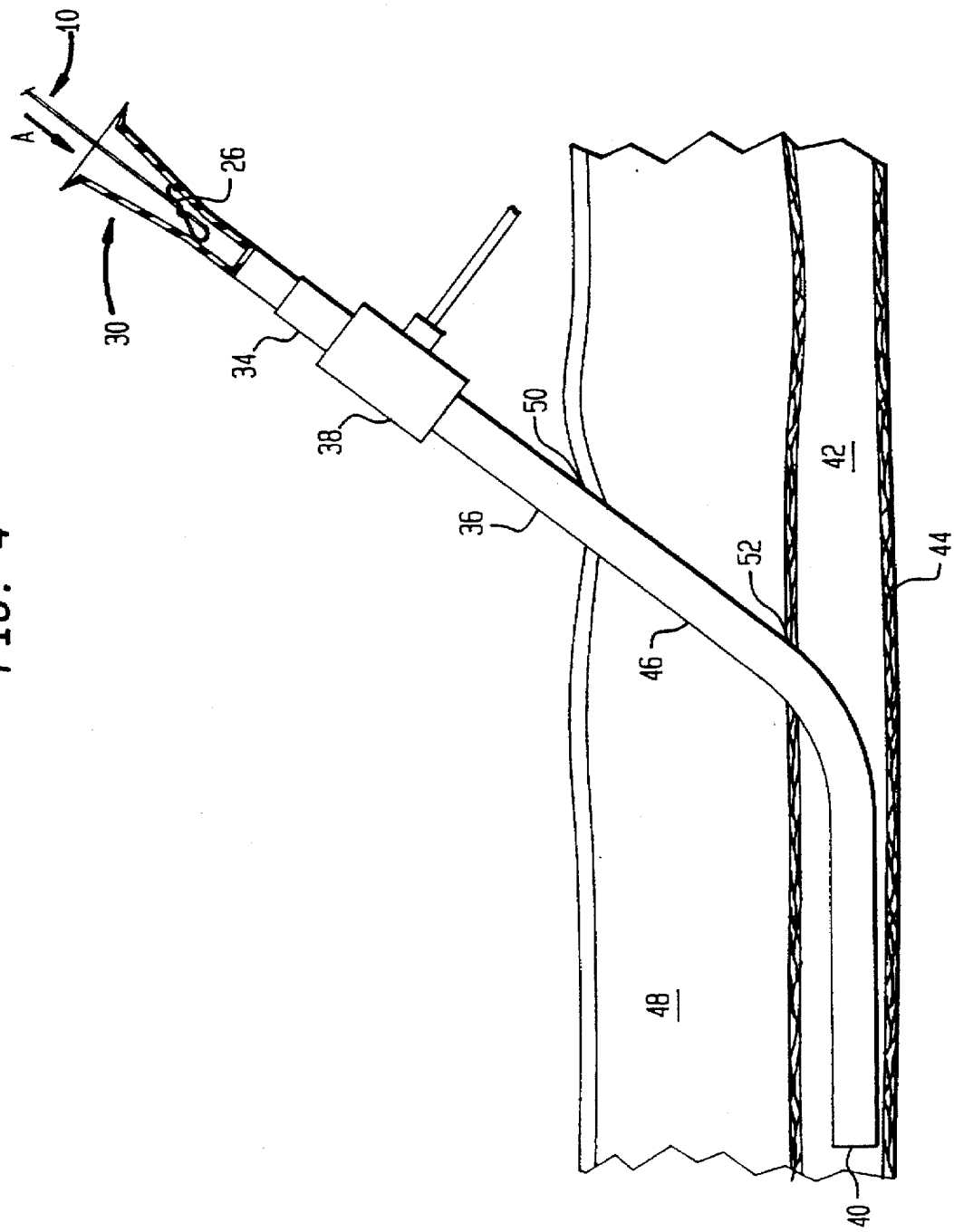

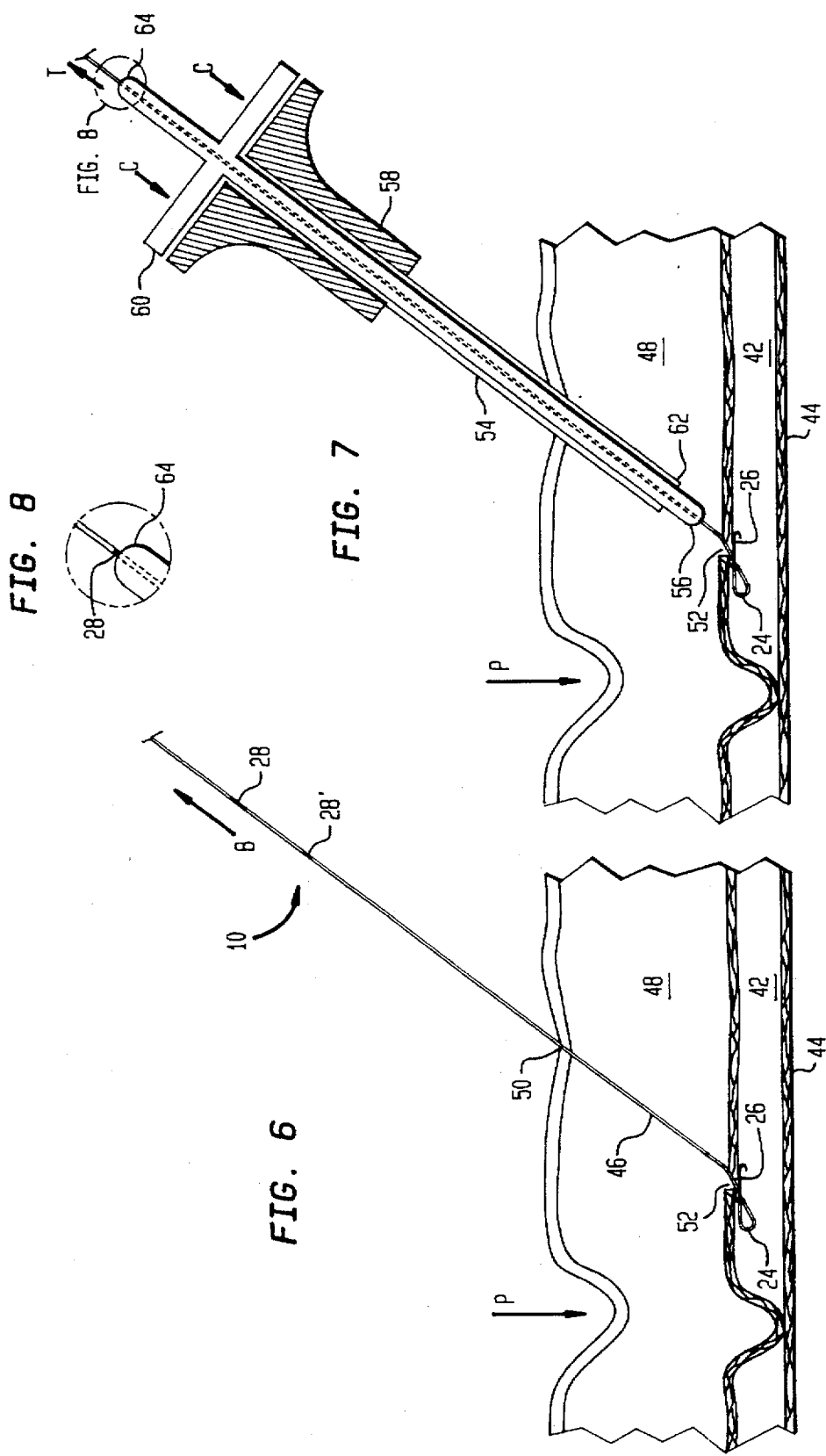

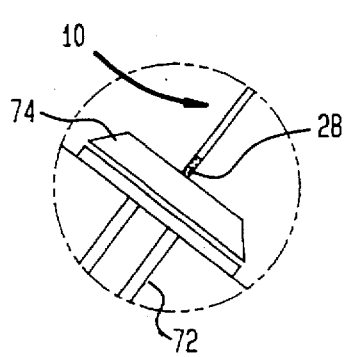
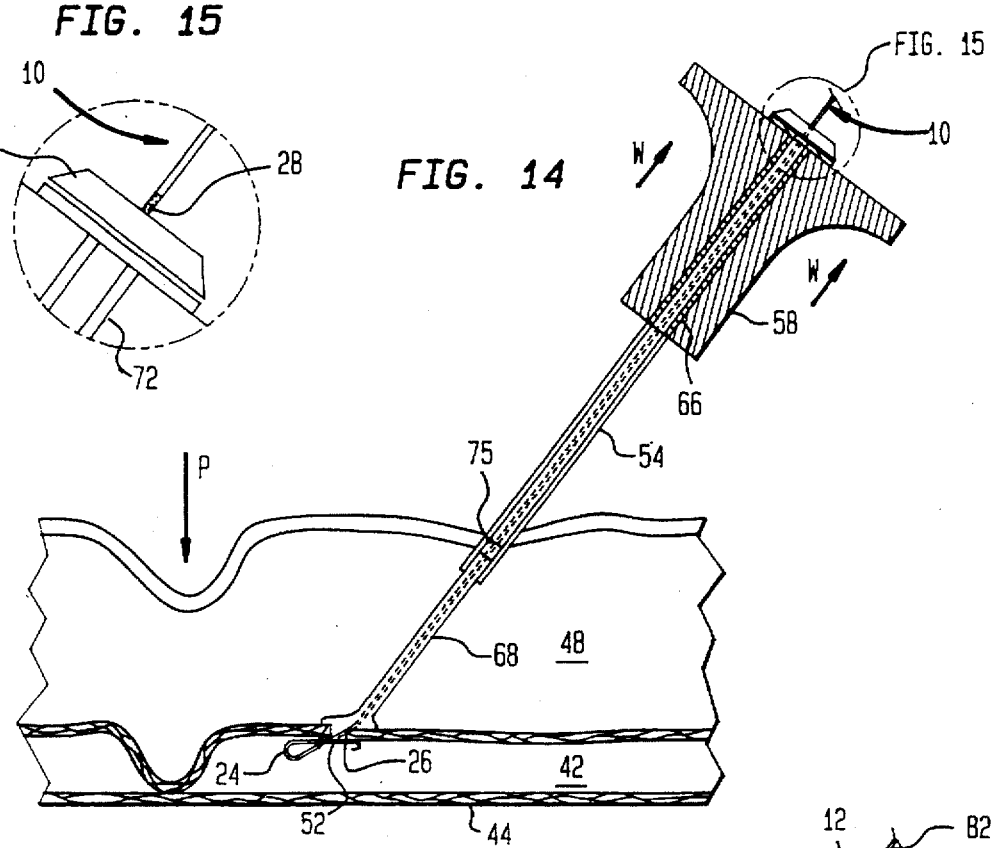
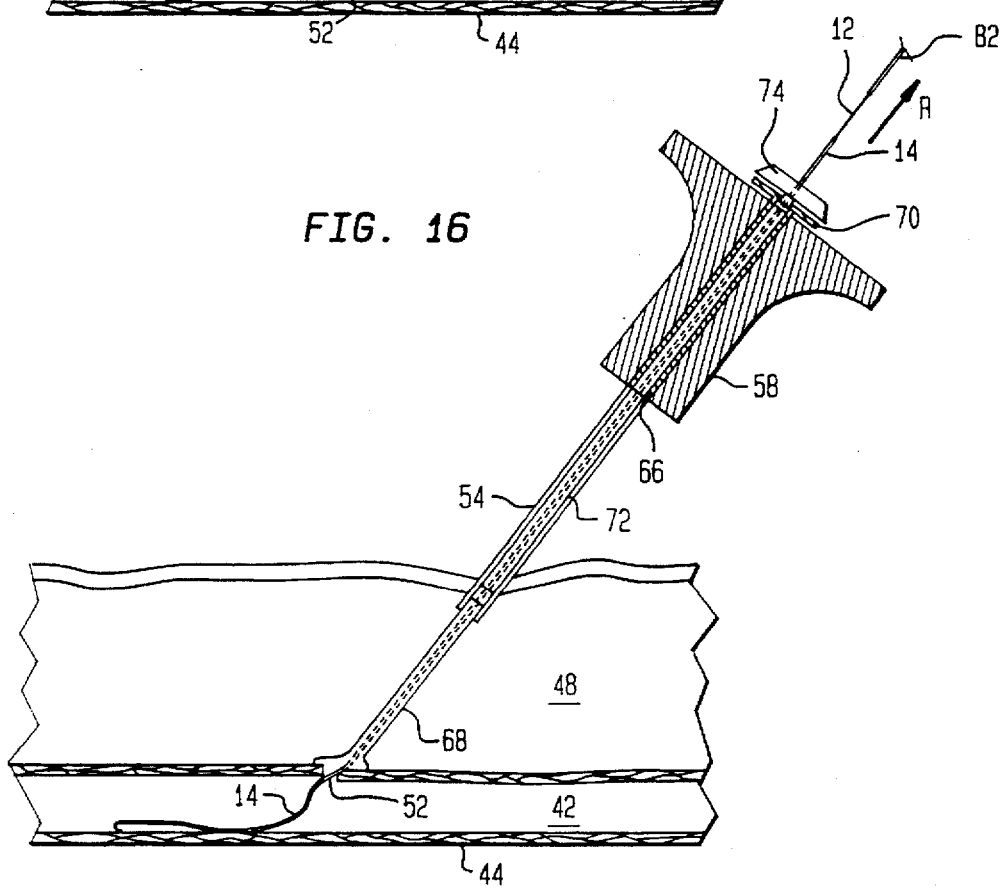

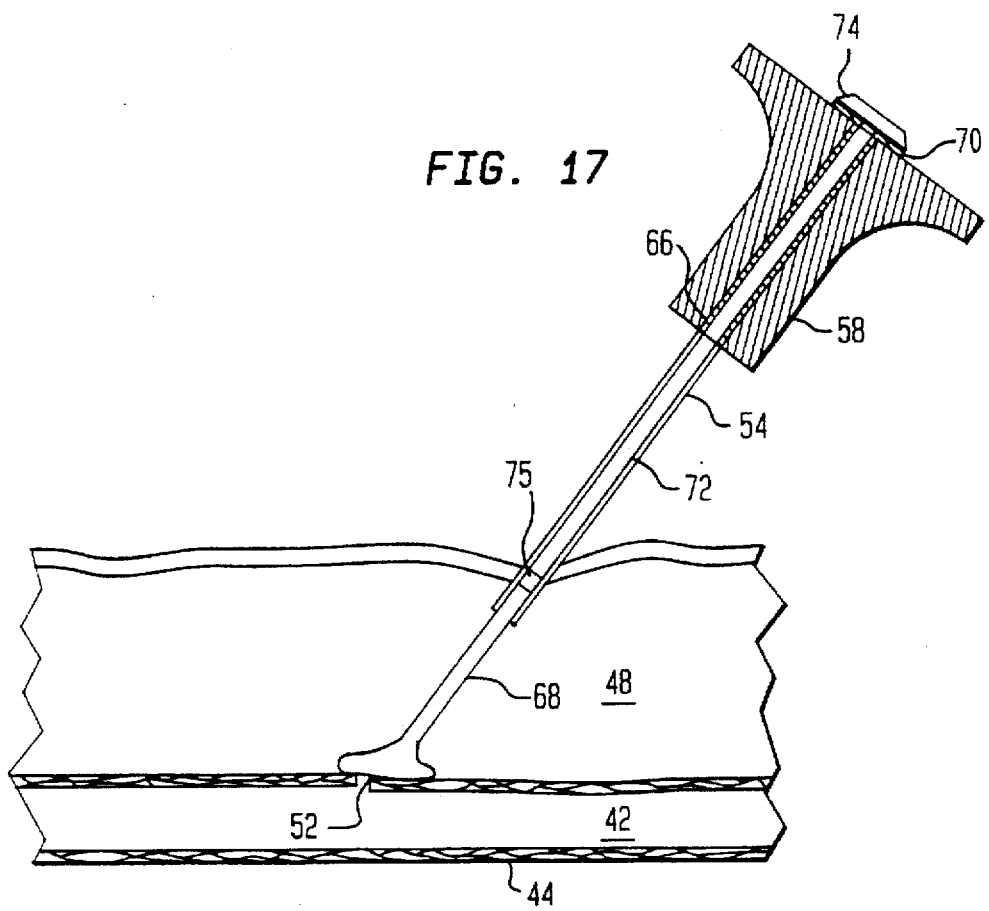
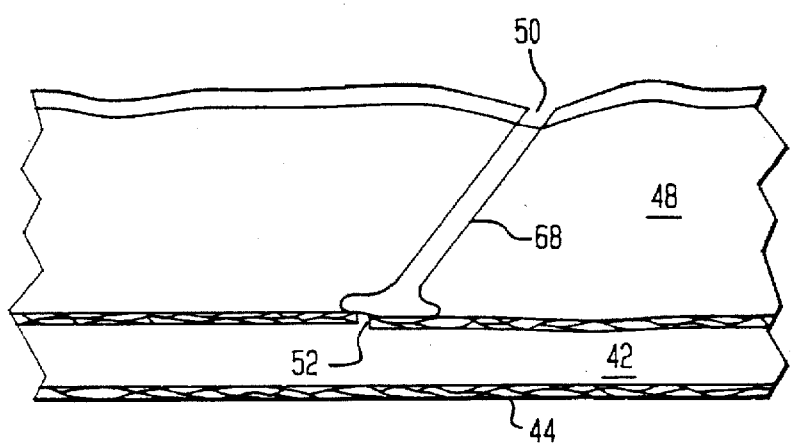

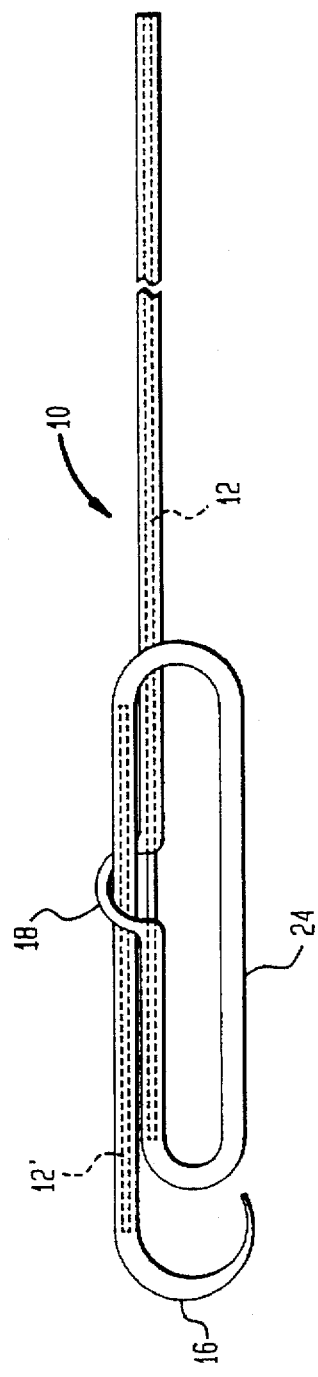
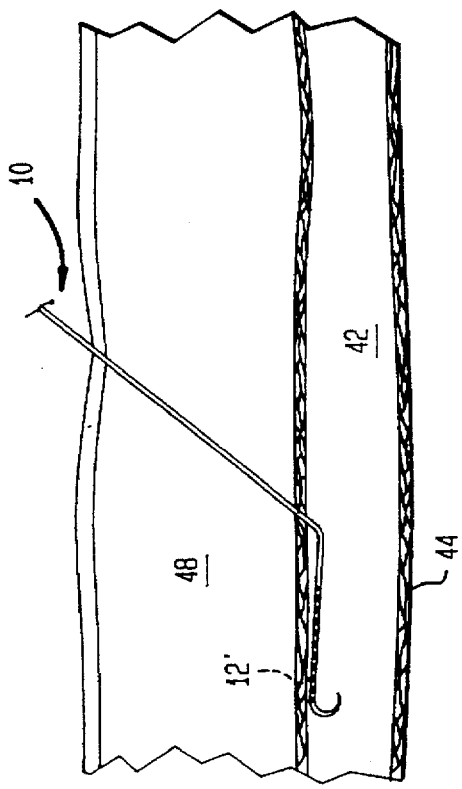
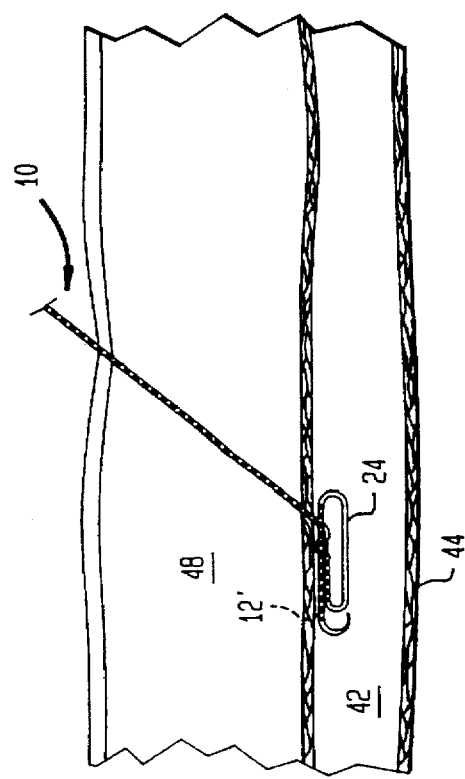

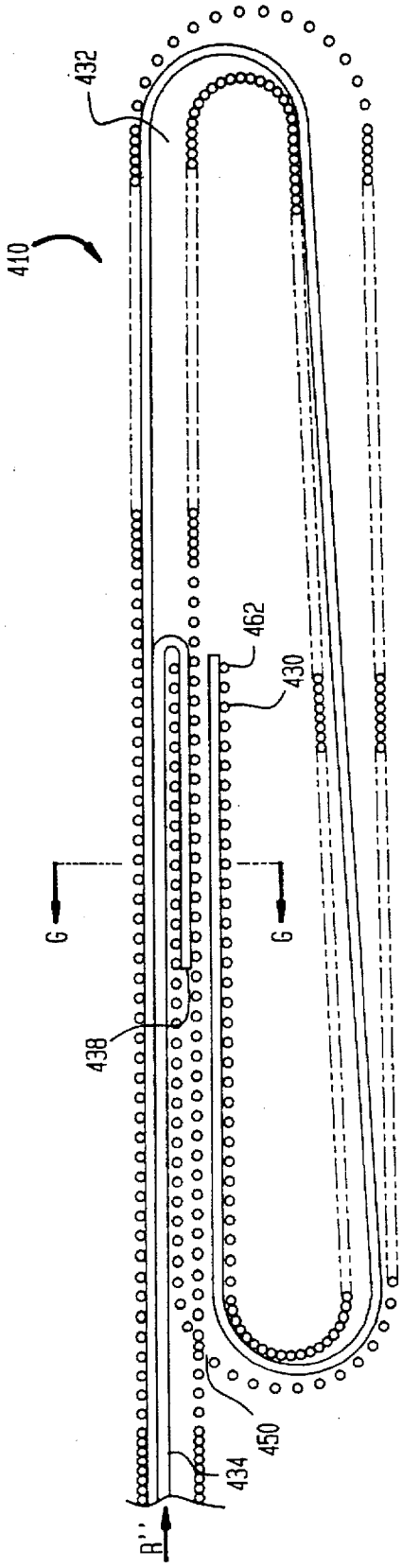
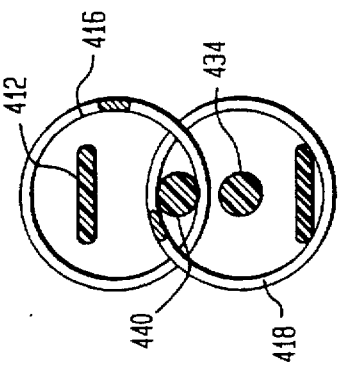
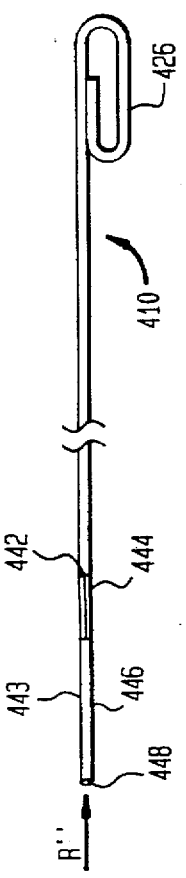
FIG. 40
FIG. 42
FIG. 41

GUIDE WIRE WITH RELEASEABLE BARB ANCHOR

This is a continuation-in-part of application Ser. No. 08/182,501 filed Jan. 18, 1994, now abandoned.

BACKGROUND OF THE INVENTION

Field of the Invention

The present invention relates to medical devices. More particularly, it relates to devices used to aid in the insertion of hemostatic materials into a wound after completion of a percutaneous procedure. It also relates to devices used for precisely locating internal punctures in arteries, veins, internal organs and the like.

Numerous medical procedures involve percutaneous insertions into a vein or artery. Among the more common are cardiac catheterization, intra-aortic balloon pumping (IABP) and percutaneous transluminal coronary angioplasty (PTCA). When such a procedure is completed, the catheter and/or sheath is removed, leaving a wound that must be repaired. The wound consists of a skin puncture, an arterial or venous puncture and a channel through the patient's tissue connecting those two punctures.

Traditionally, repair was accomplished either by application of pressure for extended periods of time or sometimes by suturing. More recently it has been found that insertion of hemostatic materials, especially collagen plugs, against the outside wall of the affected artery or vein produces better results, more rapidly and with less discomfort to the patient. One such procedure, and a device for practicing that procedure, is described in U.S. Pat. No. 5,391,183, assigned to the assignee of this application, the contents of which are incorporated herein by reference.

Since clots within the blood stream are extremely undesirable, it is important that the insertion of collagen be done in such fashion as to avoid forcing it through the arterial puncture. Several devices have been developed in an attempt to accomplish this objective. For example, U.S. Pat. Nos. 4,744,364, 4,852,568, 4,890,612, to Kensey propose an umbrella-like structure permanently placed in the vessel to seal the arterial wound from the inside. Another approach is described in U.S. Pat. No. 5,108,421 wherein a balloon is placed inside the arterial lumen, expanded until it is larger than the wound, and then pulled back against the wall of the artery to act as a temporary seal and stop to prevent further plug advancement.

A different approach to preventing entry of collagen into the artery can be found in previously noted U.S. Pat. No. 5,391,183. That patent teaches use of a collagen guide sheath which is larger in diameter than the vessel puncture. The sheath, because it is oversized, cannot pass through the vessel puncture so as to enter the lumen. Upon insertion of such a guide sheath, the physician can tell when the distal end reaches the vessel wall simply by tactile sensation. The collagen, which is inside the sheath, is then held in place at the outer wall of the vessel while the sheath is withdrawn.

SUMMARY OF THE INVENTION

The instant invention provides a new and improved system for using an hemostatic plug, generally collagen, to close a percutaneous wound. Such a plug might act by chemical interaction with the blood or might simply be a mechanical hemostat that physically blocks the flow of blood, or it might be a plug that combines these two mechanisms of action. The invention permits precise and definitive location of the plug adjacent the arterial puncture but outside of the arterial lumen and leaves no foreign body in the lumen when the procedure has been completed. The invention, however, is not directed to the plug, but rather to a new insertion guide wire which can be used to facilitate insertion of such plugs and which can be used for other purposes as well.

In its simplest form, the instant invention involves the use of an insertion guide wire which has a releasable anchor at its distal end. During insertion, according to the preferred procedure, the anchor is passed through the introducer sheath used during the percutaneous procedure. This original introducer sheath will be referred to hereinafter as the "procedural sheath". Upon exiting from the distal end of the procedural sheath, the anchor is within the arterial lumen. As the procedural sheath is then withdrawn, the insertion guide wire is partially retracted until the anchor catches on the inside wall of the artery at the puncture. The anchor prevents complete retraction of the insertion guide wire. The collagen or other hemostatic material can then be passed over the insertion wire directly to the vessel exterior at the puncture site.

Another feature of the anchor is that it permits precise determination of the location of the vessel puncture. By use of a reference mark placed at a known distance from the anchor, the location of the vessel puncture is always known, irrespective of movement of the patient and irrespective of pressure applied in the vicinity of the insertion site.

In the preferred method of practicing the instant invention, after the procedural sheath is withdrawn, a guide sheath/dilator set is passed over the insertion guide wire until the distal tip of the guide sheath is just outside of the arterial puncture. The dilator is then removed and an insertion tube or canister, preloaded with collagen, is slid down into the proximal end of the guide sheath. A plunger is then used to force the collagen plug from the preloaded canister into and through the guide sheath. When the collagen reaches the exterior of the artery wall, its distal end is slightly compressed. In this condition the physician holds it in place with the plunger, and withdraws the guide sheath, thereby exposing the rest of the collagen to the blood from the artery and the surrounding tissue. Then, while still holding the collagen in place, the anchor is released and the insertion guide wire removed, leaving no foreign body inside the arterial lumen. The collagen remains outside the artery to seal the puncture.

While it is anticipated that the most immediate and widespread use of the present invention will be in connection with sealing percutaneous wounds in femoral arteries, it has many other applications as well. For example, the blood vessel being sealed need not be the femoral artery or, for that matter, any artery at all. It could just as well be a vein. Also, it need not be used only in situations where sealing is required. Rather, it can be used merely for its ability to provide a precise location of any internal puncture. It could find utility in connection with locating and/or sealing punctures in internal organs, perhaps as an adjunct to laparoscopy. Accordingly, the term "artery" is used herein in a very broad sense to encompass arteries, veins, internal organs and the like.

Disclosed herein are three basic types of releasable anchors. The first is a loop anchor which is formed by turning the distal tip of the insertion wire back upon itself so as to cross the main body of the wire, with the distal tip then forming a pig tail. The second type of anchor is formed by use of a soft-tipped barb that protrudes from the insertion wire sheath slightly proximal to the distal end. The third type of releasable anchor according to the present invention is comprised of an elongated overlapping loop at the distal end wherein the overlapping loop sections are comprised of interleaved coils. Described below are all three embodiments as well as several alternative versions thereof.

BRIEF DESCRIPTION OF THE DRAWINGS

FIG. 1 shows an anchor loop insertion wire comprised of a core wire and sheath suitable for use in practicing the instant invention.

FIG. 2 shows the insertion wire of FIG. 1 with its distal end formed into a loop.

FIG. 3 shows the insertion wire of FIG. 2 with the loop portion thereof within the confines of an insertion funnel.

FIG. 4 shows the loop and funnel assembly of FIG. 3 inserted into the proximal end of a procedural sheath.

FIG. 6 shows the insertion wire in a percutaneous wound, after removal of the procedural sheath with the wire having been partially withdrawn so that the loop anchor engages the inside of the artery wall.

FIG. 7 shows the insertion wire as in FIG. 6 with a guide sheath/dilator set having been slid down over the wire into the wound.

FIG. 8 is an exploded view of the proximal end of the dilator when properly seated in the wound.

FIG. 14 shows the collagen plug of FIG. 10 having been pushed by the plunger through the guide sheath and the guide sheath having been withdrawn from the wound.

FIG. 15 is an exploded view of the proximal end of the plunger when the collagen plug is properly seated in the wound.

FIG. 16 shows the core wire of the insertion wire having been partially withdrawn so as to release the loop at the distal end.

FIG. 17 shows the insertion wire having been removed while the guide sheath, plunger and collagen plug are held in place.

FIG. 18 shows the wound with the collagen plug in place after the plunger and guide sheath have been withdrawn.

FIG. 22 shows yet another embodiment of an insertion wire formed into still a different kind of anchor loop.

FIG. 23 shows the anchor loop of FIG. 22 inside an artery.

FIG. 24 shows the insertion wire of FIG. 23 after the anchor loop has been released.

FIG. 40 is a cross sectional view of the distal portion of the insertion guide wire of FIG. 38 fully assembled with the locking core wire in place.

FIG. 41 is a plan view of the insertion guide wire of FIG. 40.

FIG. 42 is cross sectional view taken along cutting line G—G of FIG. 40.

DETAILED DESCRIPTION OF THE PREFERRED EMBODIMENT

Figure 5:
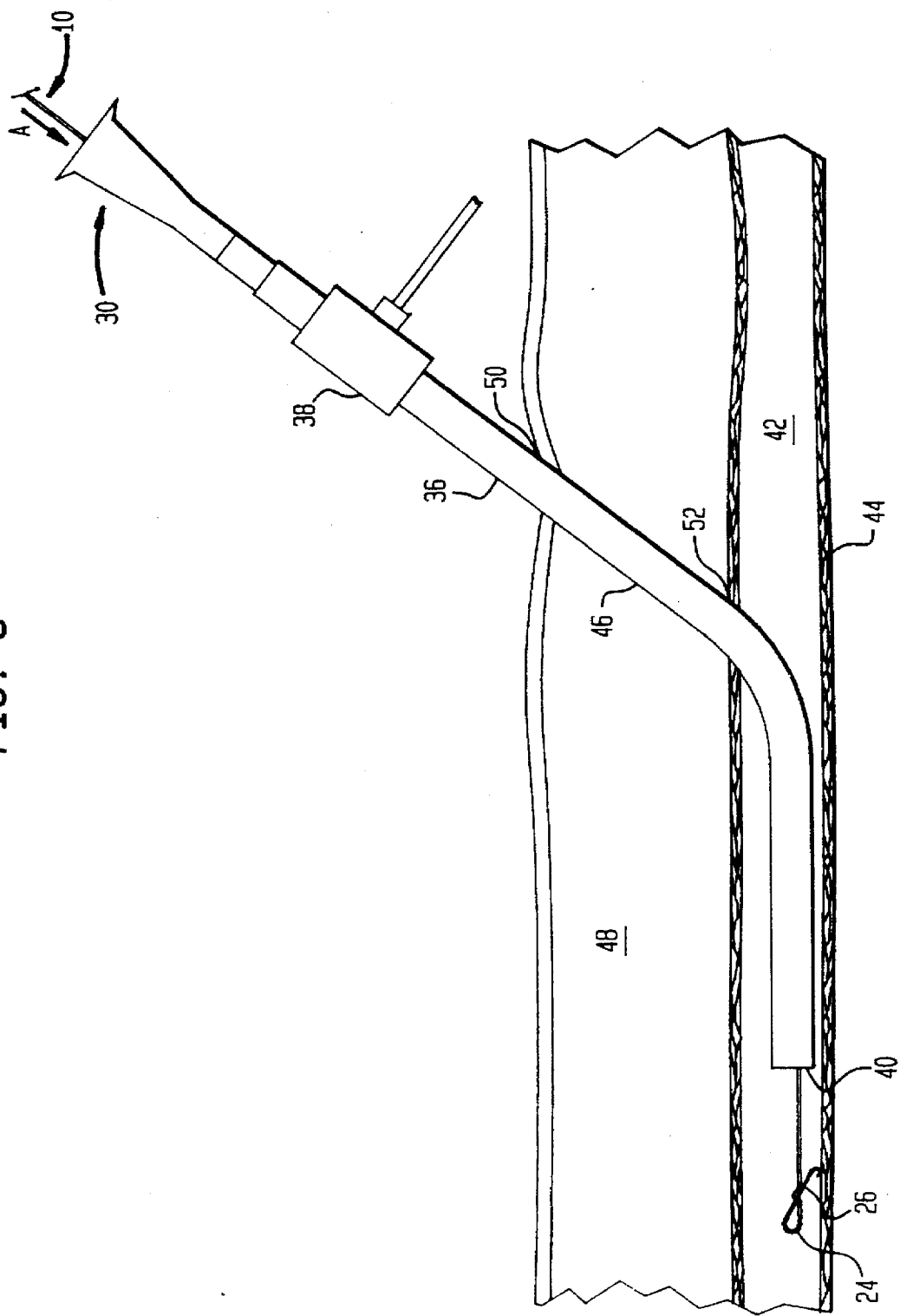
FIG. 5 shows the insertion wire having been passed through the funnel, through the procedural sheath and into an artery.
Figure 9:
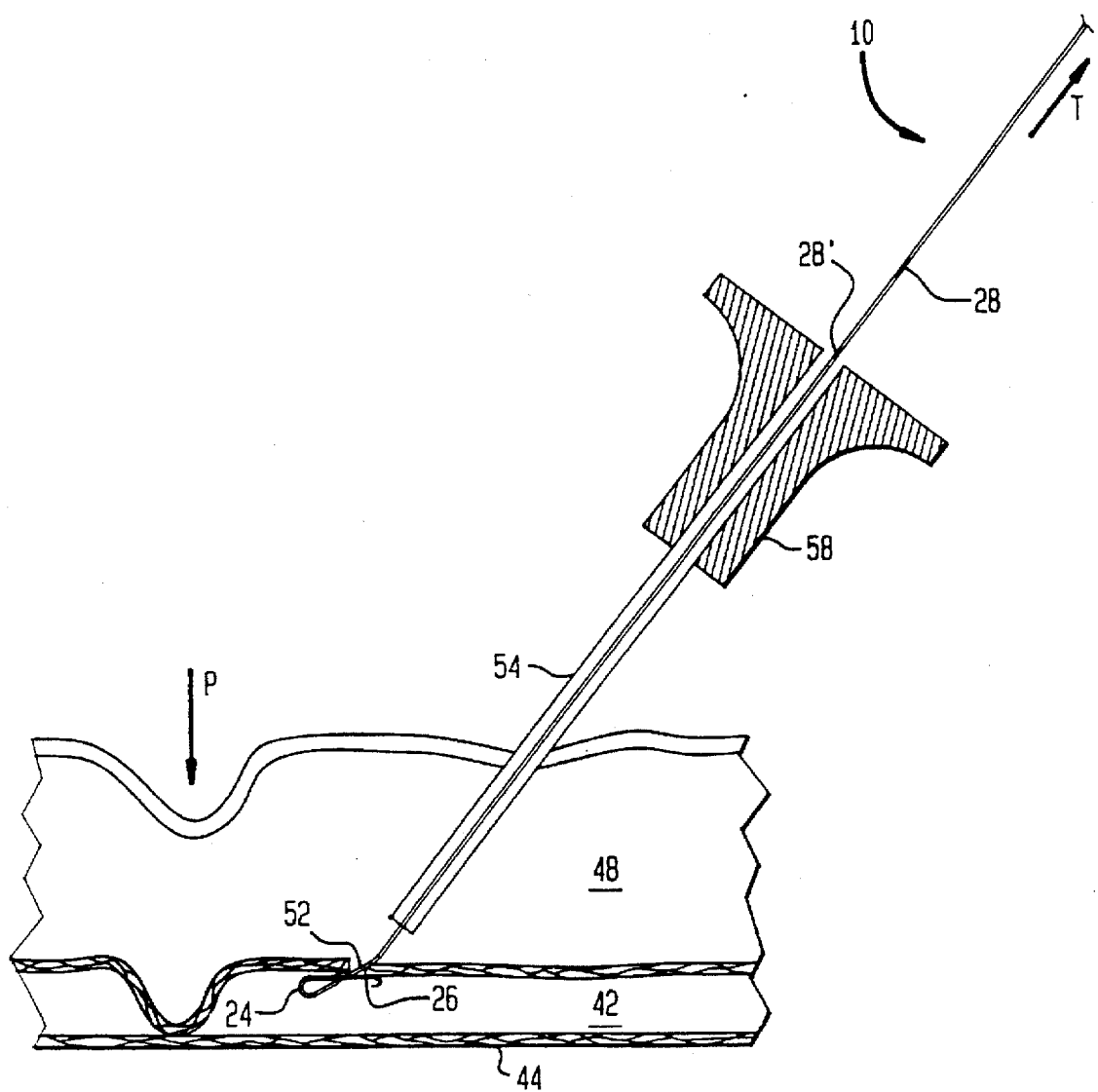
FIG. 9 shows the insertion wire and guide sheath as in FIG. 8 with the dilator having been removed.
Figure 10:
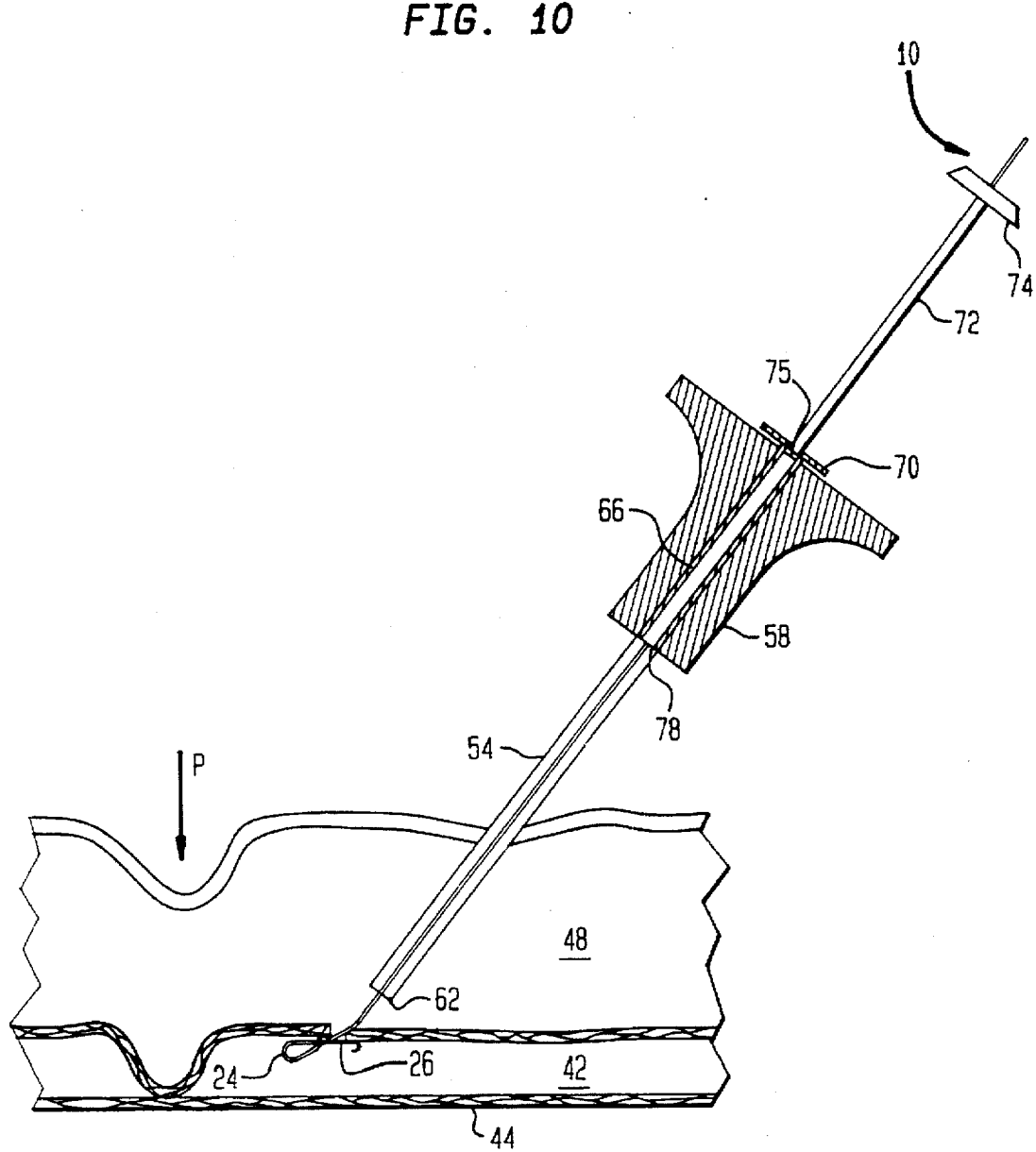
FIG. 10 shows a collagen cartridge and plunger assembly seated in the proximal end of the guide sheath.

Referring to FIG. 1, there is depicted an insertion wire 10 comprised of a core wire 12 slidably encased within a core wire sheath 14. The distal end 22 of insertion wire 10 may be provided with a J-tip 16. About two and a quarter inches or so proximal of J-tip 16, sheath 14 has been slit, perhaps only for a distance of between ⅛" and ¼".At the slit, the sheath can be caused to buckle or form a bulge or notch 18 leaving a gap 20 between the core wire 12 and the slit portion of the sheath which forms notch 18.

The core wire 12 and sheath 14 should be made of biocompatible materials. For example, the wire may be of a nickel titanium alloy and the sheath may be polyethylene. The sheath may also be formed of a metal coil. It has been found that to pass through a 8 Fr. introducer, wire sheath 14 can have an o.d. of about 0.030" and an i.d. of 0.015", while the core wire can have an o.d. of between 0.010" and 0.012".

The distal tip of the insertion wire is then bent back and inserted through gap 20, forming an anchor loop 24. In this configuration, as best seen in FIG. 2, the distal end 22 of insertion wire 10 and J-tip 16, both of which have passed through gap 20, together act as a pigtail 26, protruding sideways from insertion wire 10 with a component normal to the major axis of the insertion wire. Once tip 16 has passed through gap 20 and the force causing bulge 18 has been released, the bent back portion of insertion wire 10 is held by friction in gap 20, between core wire 12 and sheath 14.

In FIG. 2 it can be seen that sheath 14 is provided with a reference mark 28. This reference mark is at a predetermined distance D from notch 18.

In preparation for use, anchor loop 24 is placed within a funnel 30 and the nose or small end 32 of the funnel is slid into the proximal end 34 of procedural sheath 36. The nose of funnel 30 is made long enough so as to pass through hemostatic valve 38 when the cone seats on the proximal end of the sheath. Although the size of funnel 30 is not critical, its length, taper and cross-section should be such as to permit sliding passage through proximal end 34 of procedural sheath 36 and through valve 38. If desired, the funnel can be provided with its own hemostatic valve (not shown) to act as a back-up when the nose penetrates the valve in the hub of the procedural sheath.

As noted above, the insertion guide wire 10 of this invention is designed, inter alia, for use following the completion of a percutaneous procedure. Normally, after the operative portion of such a procedure has been completed, the procedure device, for example, the PTCA catheter, is removed, leaving the procedural sheath 36 in place (as best seen in FIGS. 4 and 5). At this point, the distal tip 40 of the procedural sheath is still in the lumen 42 of vessel 44, while the body of procedural sheath 36 passes through wound channel 46 in the patient's subcutaneous tissue 48 and out through skin puncture 50. The insertion guide wire 10 is then pushed, in the direction of arrow A, until the anchor loop 24 and pigtail 26 have exited from distal tip 40 of sheath 36 into lumen 42 of artery 44.

With the procedural sheath in place, digital pressure P is applied to artery 44 upstream of puncture 52 and procedural sheath 36 is then withdrawn. Because insertion wire 10 passes through hemostatic valve 38, as procedural sheath 36 is being withdrawn, it tends to drag insertion wire 10 along with it. Wire 10 is retracted, either by the dragging action of hemostatic value 38 or, failing that, by the operator, until anchor loop 24 and pigtail 26 catch on the inside of the artery wall (see FIG. 6). Anchor loop 24 catches on one side of arterial puncture 52 and pigtail 26 catches on the other side, preventing further withdrawal of the insertion wire. Continued withdrawal of the procedural sheath causes the hemostatic valve 38 to slide over insertion wire 10 until the entire procedural sheath has been removed from the wound, leaving only the distal portion of insertion wire 10 in lumen 42 of artery 44. The remainder of insertion wire 10 runs from there, through arterial puncture 52, through tissue channel 46 and out through skin puncture 50.

As can be seen, when insertion wire 10 is pulled back so that anchor loop 24 and pigtail 26 impinge on the inside of the wall of artery 44, notch 18 is at arterial puncture 52 and reference mark 28 is, therefore, at distance D, a predetermined known distance from puncture 52.

While maintaining slight tension T on wire 10, a guide sheath 54/dilator 56 set is slid down, in the direction of arrows C, over insertion wire 10 until reference mark 28 can be seen emerging from the proximal end 64 of dilator 56. Although shown as a single stripe, other configurations may also be used. For example, the reference mark 28 may actually be made up of several, axially displaced stripes of different colors or different thicknesses or different darknesses or different separations or the like, to warn the physician that the distal-most portion of the reference mark is approaching.

Sheath 54 is provided with handle 58 and dilator 56 is equipped with finger wings 60. To assemble the integrated sheath/dilator set, dilator 56 is slid down into sheath 54 until finger wings 60 abut the proximal end of handle 58. Dilator 56 is then turned ¼ turn to the right to lock the dilator and sheath together as an integrated unit. When they are locked together, finger wings 60 and handle 58 are aligned, thereby forming a combined handle for the set.

Once reference mark 28 emerges from the proximal end 64 of dilator 56, the sheath is fully inserted. In this position, the physician can be confident that distal tip 62 of guide sheath 54 is adjacent but outside of arterial puncture 52 because the sheath/dilator set has been selected so that the distance from the proximal end 64 of dilator 56 to distal tip 62 of guide sheath 54 is slightly less than distance D. If, as taught in U.S. Pat. No. 5,391,183, an oversized sheath/dilator set is used, when the distal tip of the dilator reaches the wall of the artery, not only will the appearance of reference mark 28 tell the physician to stop, so too will the tactile sensation which is experienced when the oversized dilator impinges against the outside wall of artery 44.

With the sheath thus properly located, and while still maintaining tension T on insertion wire 10, dilator 56 is rotated ¼ turn to the left to unlock it from sheath 54 and finger wings 60 are used to withdraw dilator 56. During withdrawal of dilator 56 and thereafter, handle 58 is used to hold sheath 54 in place. To assist in keeping sheath 54 in place, a second reference mark 28' may be placed on wire 10.

Figure 11:
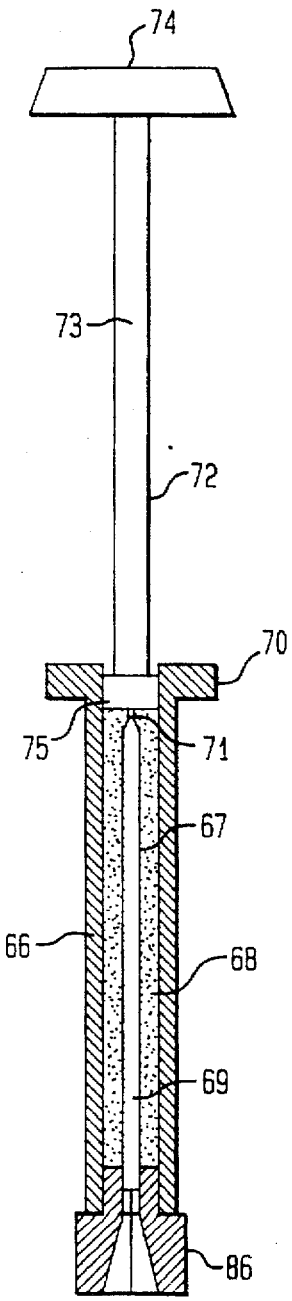
FIG. 11 shows, in cross-section, the assembled and fully charged collagen cartridge.
Figure 12:
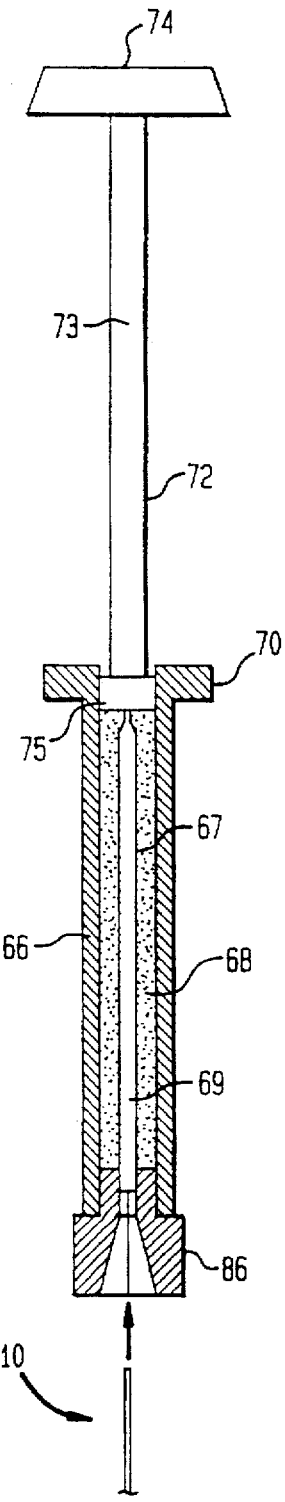
FIG. 12 shows, in cross-section, the insertion guide wire being fed into the distal end of the collagen cartridge.
Figure 13:
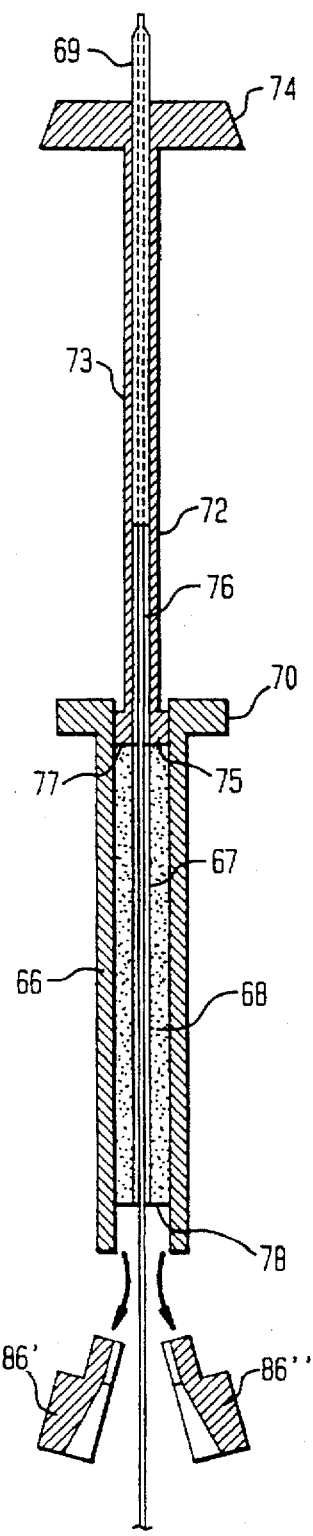
FIG. 13 shows, in cross-section, the collagen cartridge of FIG. 11 after the split halves of the retaining cone have been ejected.

A canister or insertion tube 66, preloaded with a collagen plug 68 is provided with a plunger 72, which has an enlarged head 74 at its proximal end, a stem 73 and a piston 75 at its distal end. Plug 68 is preferably made with a through lumen 67 in which is seated plug threading tube 69. At its proximal end 71, tube 69 is sealed. In order to facilitate insertion of the proximal end of wire 10 into the lumen of the collagen plug, an inverted cone 86, split into two halves 86' and 86", is fitted into the distal end of the canister (see FIG. 11). Cone 86 provides a widemouth opening which leads the proximal end of wire 10 directly into the lumen of the collagen plug (FIG. 12). Once cone 86 has served its purpose, a slight flick of the finger dislodges it from the canister, permitting the two halves 86' and 86" to separate and fall away (FIG. 13).

After the proximal end of wire 10 has properly entered tube 69, wire 10 is pushed proximally through plug 68. Because the proximal end 71 of tube 69 is sealed, as the proximal end of wire 10 is pushed through and out of plug 68, it carries tube 69 with it (FIG. 13).

Canister 66 is then slid down over insertion wire 10 and into handle 58 until stop collar 70 seats against the proximal end of handle 58. Plunger 72, also having a through lumen 76, is then used to force plug 68 from canister 66 into guide sheath 54 and through sheath 54 to its distal tip 62. When plunger 72 is fully inserted (see FIG. 14), enlarged head 74 seats against the proximal face of stop collar 70. The length of the plunger is chosen so that when head 74 is seated against stop collar 70, the distal face 77 of piston 75 is slightly distal to tip 62 of sheath 54.

In addition, the plunger/collagen plug combination is chosen so that the distance from the proximal face of head 74 to the distal face 78 of collagen plug 68 is equal to or just slightly less than the length of dilator 56. Therefore, as plunger 72 is pushing plug 68 through guide sheath 54, when reference mark 28 emerges from plunger head 74 (see FIG. 15), the physician knows that the collagen plug is adjacent, but outside of arterial puncture 52.

It should also be noted that anchor loop 24 and pigtail 26 also help insure that the collagen stays outside of the artery. Together, loop 24 and pigtail 26 act as a physical barrier across puncture 52.

Thereafter, while holding plunger 72 steady, pressure is applied to handle 58 in the direction of arrows W. This causes the sheath 54 to be withdrawn from around the collagen plug, leaving the collagen plug to seal arterial puncture 52 and fill wound channel 46. After waiting for approximately 30 to 60 seconds to permit the collagen to begin reacting with the blood, pressure P can be removed from the artery.

As noted earlier, insertion wire 10 is comprised of a core wire 12 and a sheath 14. Sheath 14, in addition to having a slit near the distal end, has a circumferential cut 80 toward its proximal end 82. Core wire 12 is slidable within the medial portion of sheath 14 from cut 80 to tip 16. However, the portion of sheath 14 which is proximal of cut 80 is affixed to wire 12. This can be accomplished by any number of means, for example, by use of adhesives, by crimping or other mechanical means or by shrink fitting. Therefore, wire 12 can be made to slide axially within sheath 14 by pushing or pulling on end 82 while holding the medial portion of sheath 14 steady.

After guide sheath 54 has been withdrawn, while holding wire sheath 14 in one hand, proximal end 82 is pulled axially in the direction of arrow R. This causes core wire 12 to slide through sheath 14 until its distal tip is proximal of notch 18, thus releasing loop 24, permitting the distal end of sheath 14 to become flaccid (see FIG. 16) and enabling sheath 14 to be withdrawn entirely from collagen plug 68 (see FIG. 17). The guide sheath 54/canister 66/plunger 72 assembly can then be removed and discarded, leaving only the collagen plug in place, as seen in FIG. 18.

While it is believed preferable to "lock" loop 24 in place by passing end 22 through gap 20, in some cases this may not be necessary. Insertion wire 10 may be provided with a preformed loop (not shown) near its distal end. This preformed loop may take any one of a multitude of different shapes. Release of the insertion wire with a pre-formed loop is accomplished simply by pulling on the proximal end of insertion wire 10. The preformed loop, which at this point is in the arterial lumen, straightens out and passes through collagen plug 68.

Figure 19:
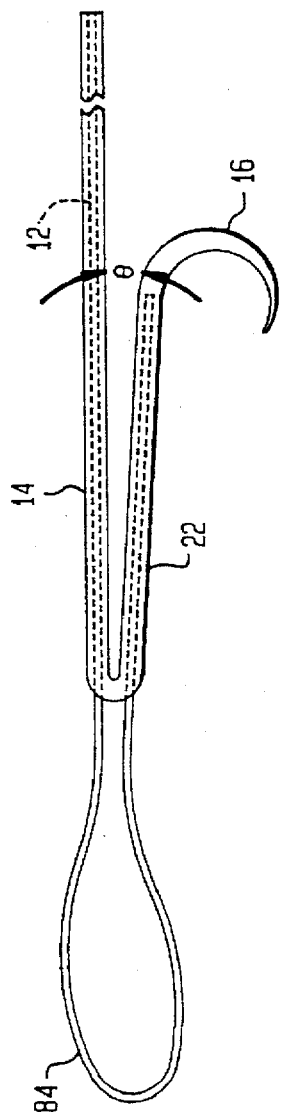
FIG. 19 shows another embodiment of an insertion wire formed into a somewhat different kind of anchor loop.
Figure 20:
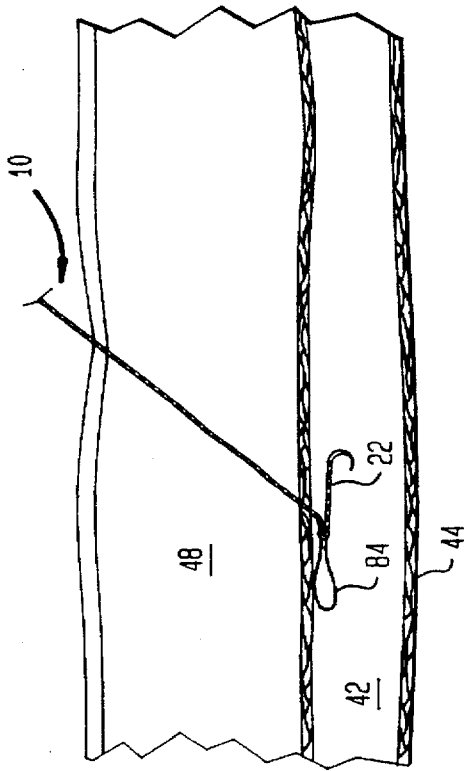
FIG. 20 shows the anchor loop of the embodiment of FIG. 19 inside an artery.

FIG. 19 shows a somewhat different form of anchor loop configuration. In this version, an intermediate portion of core wire 12, near its distal end, has been pulled out of the slit to form loop 84. However, in this configuration there is no bending back of end 22 so as to pass through a notch. Pulling an intermediate portion of wire 12 out through the slit causes sheath 14 to form angle θ less than about 180° at the slit. When this configuration is used, loop 84 catches on one side of the arterial puncture and end 22 catches on the other side, as shown in FIG. 20.

Figure 21:
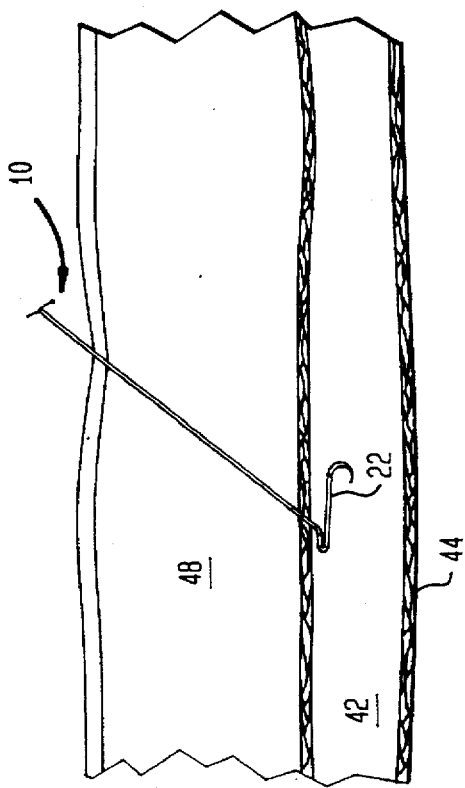
FIG. 21 shows the anchor loop of FIG. 20 with the core wire withdrawn.

Although the manner of forming the loop in FIG. 19 is somewhat different from that of the first version, the end result is substantially the same. The guide wire is placed in a funnel, inserted through a procedural sheath into the artery and then pulled back until the loop 84 and end 22 catch and act as an anchor. To release the anchor of the FIG. 19 embodiment, the core wire 12 is pulled in the direction of arrow R. This causes loop 84 to get smaller and smaller until that section of the core wire reenters the slit (see FIG. 21) permitting easy withdrawal of wire 10.

Yet another version of an anchor loop configuration is depicted in FIG. 22. In this version, core wire 12 does not reach all the way to the distal end of insertion wire 10. Instead, it ends short of the distal end and a second core wire, 12' extends from the distal end proximally toward the main core wire. Since a space can be (but is not necessarily) left between the ends of wires 12 and 12', this embodiment permits a sharper bend than the prior embodiments without putting a kink in wire 12 that might prevent its withdrawal. This embodiment, therefore, might prove to be useful for insertion through small diameter introducer sheaths.

In the FIG. 22 version, end 22 is passed through notch 18 to make a complete circle or oval. When inserted through the procedural sheath, one portion of the oval or circle catches on one side of puncture 52 and the opposite portion catches on the other side, as shown in FIG. 23.

To release the anchor loop of this version, one simply pulls on the proximal end of core wire 12 while holding sheath 14 steady. This causes the distal tip of core wire 12 to move proximally until it no longer bridges notch 18. There is then nothing to hold loop 24' in any sort of loop configuration. Instead, it is free to straighten out as insertion wire 10 is withdrawn further, passing through and out of collagen plug 68. Notice, in this embodiment, the distal segment 12' of the core wire remains within sheath 14 and when the latter is withdrawn, wire 12' comes out with it.

As those skilled in the art will recognize, guide wires are often constructed of a core wire and a ribbon wire, with both being encased within a wire coil sheath. If a guide wire of this type were used to fabricate, for example, the embodiment of FIG. 22, the core wire would be divided into two pieces 12 and 12', but the ribbon wire (not shown) and the surrounding coil (not shown), which would remain intact, would bridge the gap between the ends of wire 12 and 12'. The two ends of wires 12 and 12' could then be soldered to the ribbon wire and or surrounding coil for additional stability.

An insertion wire of this structure could be used to practice the instant invention, for example, by having the ribbon wire and surrounding coil, in the region of the gap between core wire segments 12 and 12', preformed into a loop. This loop, once inside arterial lumen 42, would then act as the anchor, and release of this preformed loop anchor would be accomplished by pulling on the proximal end of insertion wire 10. Such a pull would cause the loop to straighten out thereby permitting easy passage through the lumen of collagen plug 68.

Alternatively, this structure could be used in the practice of the present invention without any preformed loop. Because wound channel 46 is at an angle to the lumen 42 of the artery 44, the stiffness of the body of the insertion wire causes that wire to assume the configuration of a gentle curve as it transitions from lumen 42 to wound channel 46. However, as the insertion wire 10 is slowly withdrawn, the distal tip of core wire segment 12 eventually reaches arterial puncture 52, whereupon the stiffness is significantly reduced because of the discontinuity between wires 12 and 12'. The insertion wire, therefore, can then make an abrupt transition by bending sharply, rather than curving gently. This rather sudden change from a gentle curve to a sharp bend would be felt by the physician. The sharp bend and the distal end 22 extending at an angle to the main axis of insertion wire 10 would then function as the anchor. This anchor configuration too would be released simply by pulling, with additional force, on the proximal end of insertion wire 10.

Figure 25:
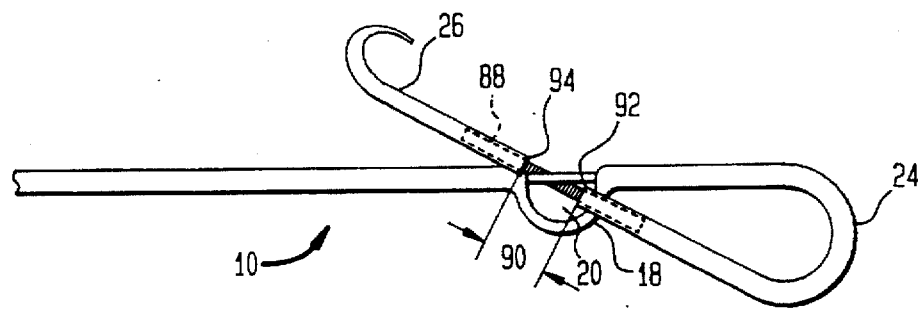
FIG. 25 shows another alternative embodiment of an insertion wire formed into an anchor loop.

FIG. 25 depicts another version of the loop anchor intended especially for passage through small (5 or 6 Fr) procedural sheaths. In this embodiment a short (generally less than about 0.3 inch) stainless steel cannula 88 is fitted into sheath 14. Sheath 14 is circumferentially split near its distal end and cannula 88 is inserted between the two portions of the sheath. The cannula can be affixed to the two pieces of sheath 14 using conventional techniques, for example, commenting, crimping, shrink fitting or the like.

As can be seen in FIG. 25, the two ends of sheath 14 do not abut. Instead, a space 90 is left between them. That space, which is bridged by cannula 88, is retained in gap 20 by virtue of shoulders 92 and 94 formed by the two ends of sheath 14.

Alternatively, cannula 88 can be placed inside sheath 14 without separating the sheath into two pieces. In this case, cuts (not shown) could be made in the top part of the sheath overlying cannula 88 and those cuts would then act as the shoulders to help keep the cannula in the notch.

It should be noted that core wire 12 need not have identical physical properties over its entire length. For example, over most of its length, where pushability is important but bendability is not, it may be made relatively stiff. This could be accomplished, for example, by using a relatively large diameter wire.

Conversely, at the distal end, pushability is of much less importance but thinness and bendability are of much greater concern. Therefore, a much thinner gauge wire can be used toward the distal end than is used over most of the body length of the insertion wire. In order to use a particularly thin and flexible wire through the bend of loop 24 and yet not have it so flexible and flaccid that it will fold over at notch 18 and pull through puncture 52, cannula 88 can be used as a reinforcing element. Ideally, when using this version, cannula 88 would bridge puncture 52 when loop 24 and pigtail 26 impinge on the inside of the artery wall.

As used herein the term "bendability" refers to the capability of the core wire to bend easily through a large angle without kinking or taking a permanent deformation or set of such magnitude as would prevent its easy withdrawal through sheath 14. The smaller the radius of bend a wire can take without kinking, the greater its bendability.

Figure 26:
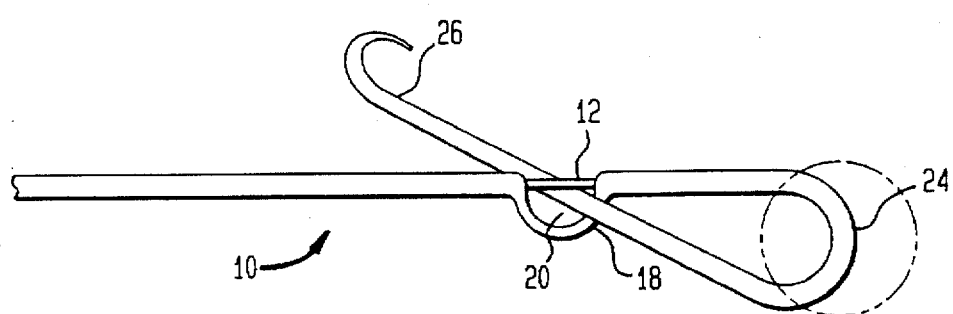
FIG. 26 is yet one more alternative embodiment of an insertion wire formed into an anchor loop.
Figure 27:
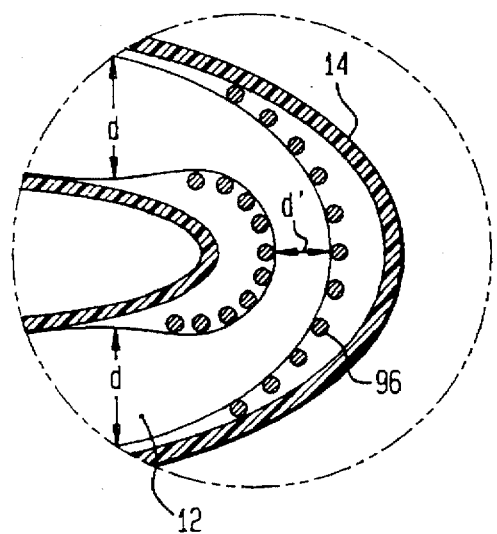
FIG. 27 is an exploded view, in cross-section, of the loop portion of insertion wire depicted in FIG. 26.

Yet another version of the loop anchor is shown in FIGS. 26 and 27. In this version, core wire 12 is ground down from diameter d, the diameter of the main body of the core wire, to diameter d', the diameter in the region where the radius of curvature of the bend is smallest. In this way, the core wire at the bend of loop 24 can be made thinner, more flexible and less liable to kink when bent to a small radius than is true of the main body of the core wire. In other words, by grinding it down the bendability is increased.

In order that the core wire in the bend have enough stiffness to open the loop up and force the pigtail out at an angle to the main axis of the insertion wire when the anchor loop emerges from the procedural sheath into the artery, a spring winding 96 may be wrapped around the ground down portion of the core wire. Winding 96 will not significantly interfere with the bendability of core wire 12 around the bend during passage through a small diameter (5 or 6 Fr) introducer or procedural sheath, but will add springability to open the loop 24 and force the pigtail 26 out at an angle when they emerge from the distal end of the procedural sheath into the arterial lumen.

It should be noted that the sheath/dilator set and canister/collagen/plunger set could be combined. Thus, the body of the canister could be made the length of the sheath, with the collagen and plunger pre-loaded therein so that the collagen is near the distal end. The distal tip of the canister sheath could be collapsed inwardly to provide a blunt nose, with radial cuts therein to permit passage therethrough of the collagen plug. This pre-loaded canister sheath combination would be slid down over the insertion wire 10 as described previously.

Although it is believed preferable to remove the procedural sheath and replace it with a guide sheath, the insertion guide wire of the present invention can also be used without a separate guide sheath. For example, it can be inserted directly into the procedural sheath. The procedural sheath can be provided with a marking (not shown) at a predetermined distance from its distal tip. After insertion of the anchor loop into the artery, the procedural sheath can be cut at its mark and then withdrawn until its cut end reaches reference mark 28 on insertion wire 10. At this point the distal tip 40 of procedural sheath has exited from lumen 42 of artery 44 and is adjacent puncture 52. The physician can then proceed as previously described.

Alternatively, the full length procedural sheath could be used. Of course, then plunger 72 would have to be made extra long so that it could push the collagen plug through the entire length of the procedural sheath.

The insertion wire of the present invention might also be used without the aid of any guide sheath at all. In that case, the collagen plug would be slid down over the insertion wire, through wound channel 46 until reference mark 28 indicates that the distal end of the collagen is adjacent to puncture 52 but is outside of artery 44.

Figure 28:
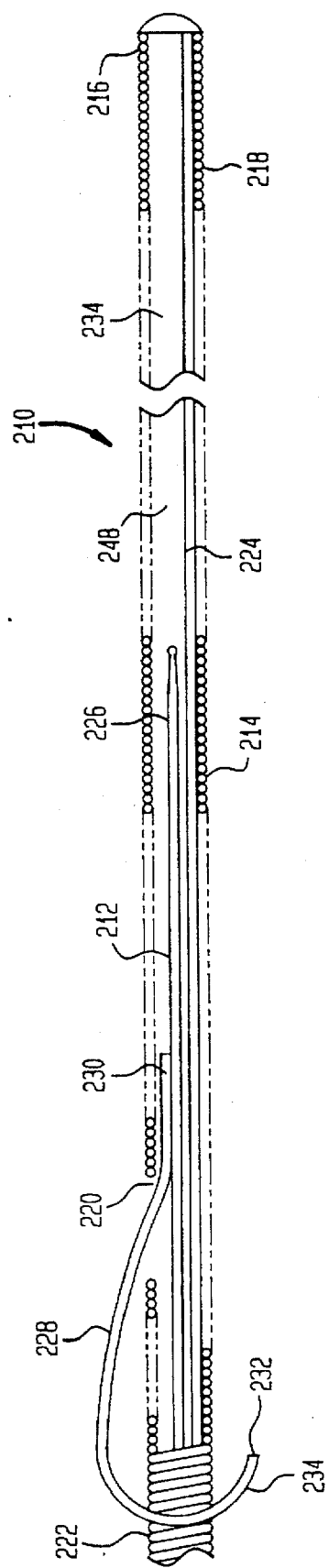
FIG. 28 shows the distal portion of an insertion wire with a barb-like anchor according to the present invention, with the anchor barb extended.

A second embodiment of an insertion guide wire with releasable anchor is shown in FIGS. 28–37. In this embodiment, the anchor is formed by use of a protruding barb. Referring to FIG. 28, there is depicted an insertion guide wire 210 comprised of a core wire 212 slidably enclosed within a core wire sheath 214. In this embodiment, the core wire sheath is comprised of a wire coil 222 of a conventional guide wire. Although not necessary, the distal end 218 of sheath 214 may be provided with a J-tip (not shown). At least about 1¾ inches and preferably about 3½ inches proximal of tip 216, sheath 214 has been provided with a notch or slit 220. This notch or slit 220 may be formed by brazing the coils 222 together in the region of notch 220 and then machining the slit into the brazed coils.

In addition to core wire, 212 sheath, 214 is provided with a safety wire 224 as is common in guide wires. Safety wire 224 is employed to provide support to the insertion guide wire 210. Core wire 212, which provides additional support to the guide wire, is tapered at its distal end 226. Attached to core wire 212, proximal to distal end 226, is the distal end 230 of wire barb 228. The proximal end of barb 228 is provided with a J tip 234. As can be seen in FIG. 28, distal end 230 of barb 228 is within lumen 248 in sheath 214 and proximal end 232 of barb 228 protrudes through notch 220.

Figure 29:
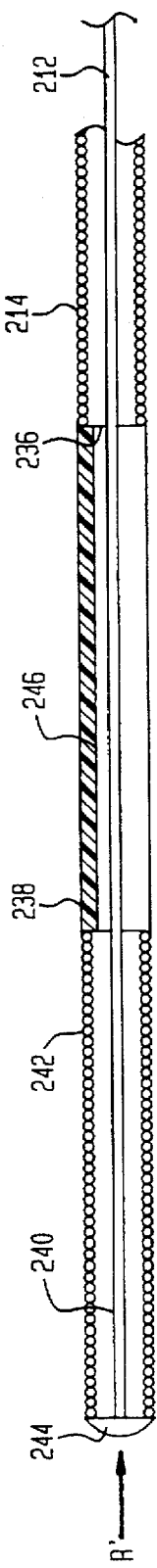
FIG. 29 shows the proximal portion of the insertion wire of FIG. 28.
Figure 30:
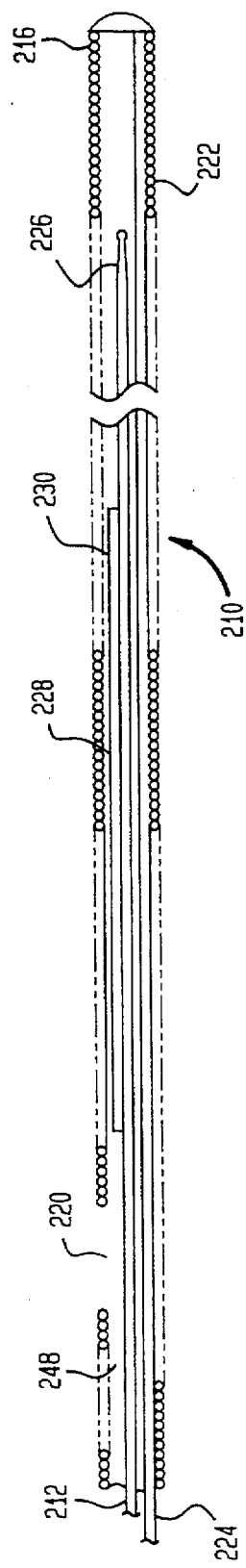
FIG. 30 shows the core wire of the insertion guide wire having been moved distally relative to the core wire sheath to retract the barb.

At the proximal end of insertion guide wire 210, core wire 212 extends beyond the proximal end 236 of core wire sheath 214 (see FIG. 29). Core wire 212 then passes through split sleeve 238 and the proximal end 240 of core wire 212 is affixed, by any number of well known means, for example, by use of adhesives, crimping, brazing or shrink fitting, to a short section of proximal coil 242. Preferably, proximal coil 242 has the same inside and outside diameters as those of core wire sheath 214. Proximal coil 242 is provided, at its proximal end, with a rounded tip 244.

Core sheath 214 may be comprised of coils of a biocompatible metal, for example stainless steel, while core wire 212 is preferably a superelastic alloy for example Nitinol and barb 228 is also preferably Nitinol or some other superelastic alloy.

The insertion wire 210 of this embodiment is inserted and used in substantially the same manner as has been described with respect to the loop anchor embodiment. Release of the anchor mechanism, however, differs somewhat.

As noted earlier, insertion wire 210 is comprised of a core wire 212, core wire sheath, 214 split sleeve, 238 and proximal coil 242. Sheath 214, in addition to having a slit near the distal end, has a lumen 248 within which core wire 212 is slidable. Since, the proximal end of core wire 212, i.e., the end which is proximal of split sleeve 238, is affixed to coil 242, core wire 212 can be made to slide axially within sheath 214 by pushing on coil 242 while holding the medial portion of sheath 214.

Absent the application of axial force in the distal direction, split sleeve 238 prevents core wire 212 from inadvertent distal movement within core wire sheath 214. When a physician applies distally directed force on proximal coil 242, initially, split sleeve 238 resists such forward movement of proximal coil 242. However, continued force applied to coil 242 causes split sleeve 238 to buckle and separate along slit 246 thereby permitting core wire 212 to move distally within core wire sheath 214.

After the guide sheath has been withdrawn, tension on the insertion wire 210 is released and insertion wire 210 is advanced slightly further into the artery, perhaps an additional 1–2 inches. Then, while wire sheath 214 is held in one hand, coil 242 is pushed axially in the direction of arrow R' (FIG. 29). This causes core wire 212 to slide distally through sheath 214 pulling barb 228 with it until the proximal tip 232 of barb 228 is inside lumen 248 of sheath 214 (FIG. 30), thus releasing the anchor and enabling insertion wire 210 to be withdrawn entirely from the collagen plug. The guide sheath/canister/plunger assembly can then be removed and discarded, leaving only the collagen plug in place.

Figure 31:
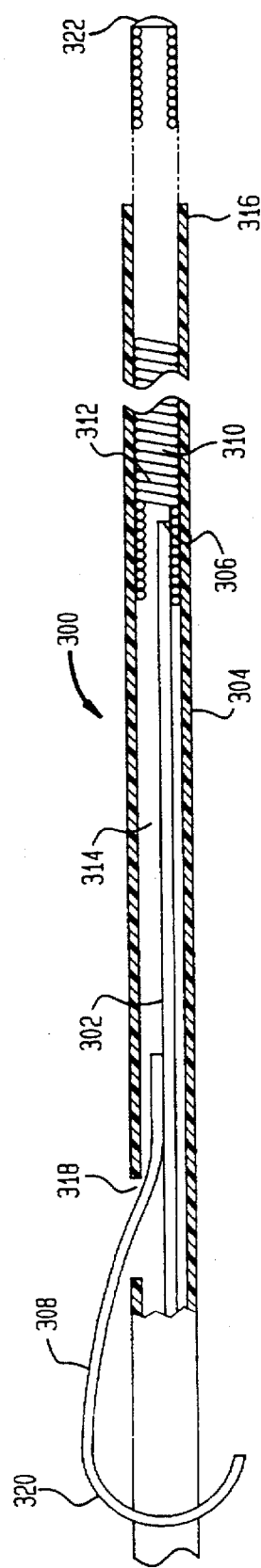
FIG. 31 shows the distal portion of a second version of the barb anchor insertion wire embodiment.

FIG. 31 shows a second version of the barb embodiment of the subject invention. The insertion wire 300 of this embodiment is comprised of a core wire 302, similar to core wire 212 of the first embodiment, a core wire sheath 304, a tip 306 and soft-tipped barb 308. The core wire sheath 304 of this embodiment is made of a biocompatible plastic, preferably polyamide tubing. As in the first version of the barb embodiment, core wire 302 is preferably made of a superelastic alloy, for example, Nitinol.

Attached to the distal tip 306 of core wire 302 is coil 310 having a distal tip 322. In the normal, preinsertion state, the proximal portion 312 of coil 310 is within lumen 314 of sheath 304.

Proximal to distal end 316, core wire sheath 304 is provided with slit or notch 318 which is sized to permit sliding passage therethrough of soft tipped barb 308. The distal portion of barb 308 is attached, for example, by brazing or spot welding, to core wire 302 and the proximal end of barb 308 is provided with a flexible J-tip 320.

In order to permit retraction of barb 308, end 312 of coil 310 is sized as to be slidable within lumen 314. Retraction of barb 308 is accomplished by exerting axial force, in the distal direction, on core wire 302.

The proximal end (not shown) of insertion wire 300 is similar to the proximal end of insertion wire 210 of the first version of this embodiment and the second version is used in the same way as the first.

Figure 32:
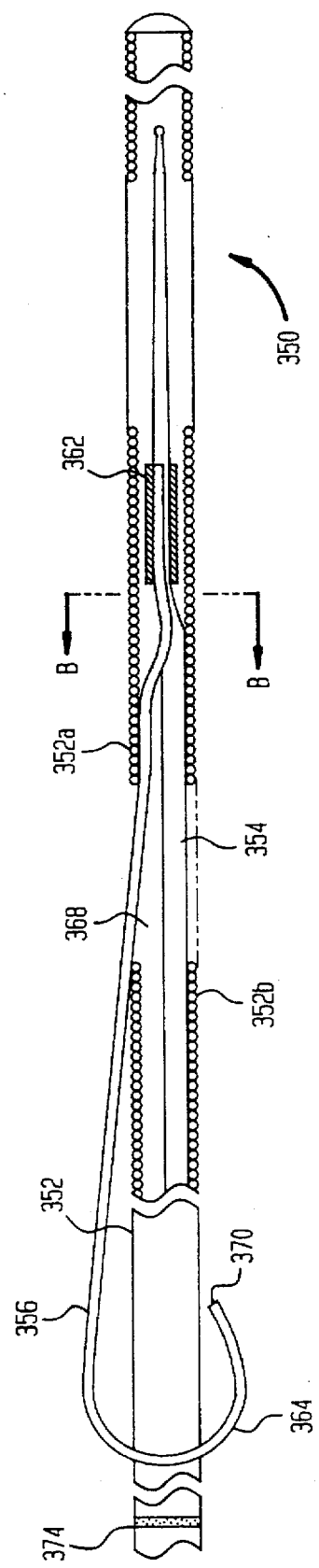
FIG. 32 is a cross sectional view taken along line A—A of FIG. 33, of the distal portion of a third version of the barb anchor insertion guide wire embodiment.
Figure 34:
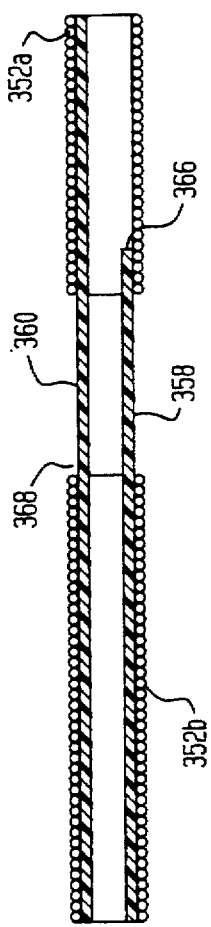
FIG. 34 is a cross sectional view taken along line C—C of FIG. 33 with the core wire removed.
Figure 33:
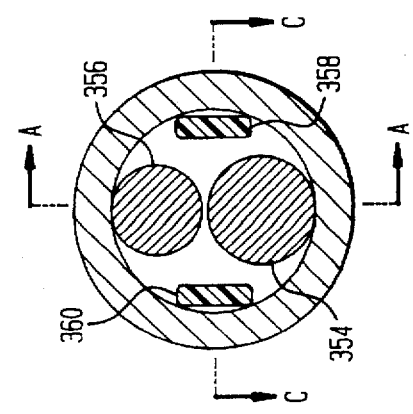
FIG. 33 is a cross sectional view taken along line B—B of FIG. 32.

FIGS. 32–34 depict a third version of the barb embodiment of the instant invention. In this version, like the version of FIGS. 28 and 29, the insertion guide wire 350 is comprised of a sheath 352, a core wire 354, a barb 356 and two safety wires 358 and 360. At its distal end, barb 356 is connected to core wire 354 by a crimp 362 and at its proximal end it is formed into J-tip 364.

Core wire sheath 352 of this embodiment is comprised of two separate sections, a distal section 352a and a proximal section 352b. Sections 352a and 352b are both brazed to safety wires 358 and 360 with notch 368 intervening between sections 352a and 352b. Although safety wire 360 reaches essentially to the distal end of the guide wire, safety wire 358 terminates at 366 just slightly past notch 368—just far enough past to ensure a good brazed joint that will help support and position section 352a.

It has been found that, because notch 368 is open around almost the entire circumference of core wire sheath 352, this embodiment of the insertion guide wire can be inserted through the guide sheath and into the artery with barb 356 fully retracted into the interior of section 352a. This is accomplished by sliding core wire 354 distally relative to sheath 352 so that crimp 362 pulls barb 356 in a distal direction until J-tip 364 straightens out and enters fully into the interior of section 352a. With the barb retracted, insertion guide wire 350 can be inserted through the procedural sheath without worrying about where in the artery the tip of that sheath is. The procedural sheath is then withdrawn, leaving the insertion guide wire 350 in place. Next, after digital pressure P is applied, guide wire 350 is slowly withdrawn until mark 374 emerges at the skin line. The emergence of mark 374 is a signal to the physician that barb 356 is in the vicinity of the arterial puncture and can be deployed. Then, core wire 354 is pulled in the proximal direction and, because there is a residual curve in barb 356, as crimp 362 is pulled proximally, tip 370 finds notch 368 and exits therethrough. Crimp 362 acts as a natural stop against the end 366 of safety wire 358 to prevent core wire 354 from being pulled too far in the proximal direction. When it is time to retract the barb so it no longer acts as an anchor, the process is just reversed.

This version, as well as the fourth version of the barb embodiment described below, is particularly well suited for a procedure wherein there is potential for snagging on side branches. It can be inserted through the procedural sheath and into the artery with the barb 356 fully retracted which is believed to be the preferred method of insertion. A marker (not shown) on the insertion wire 350 can be employed to tell the physician that notch 368 has passed the tip of the procedural sheath and has entered the artery. Then, both the insertion guide wire 350 and the procedural sheath can be withdrawn together until the tip of the procedural sheath is just slightly beyond the arterial puncture as indicated by a mark (not shown) on the procedural sheath. Alternatively, the sheath can be withdrawn first, followed by withdrawal of guide wire 350 until mark 374 emerges at the skin line. Then, with full assurance that there are no longer any side branches between notch 368 and the arterial puncture, barb 356 can be deployed without fear that it will hang up on a side branch.

Figure 35:
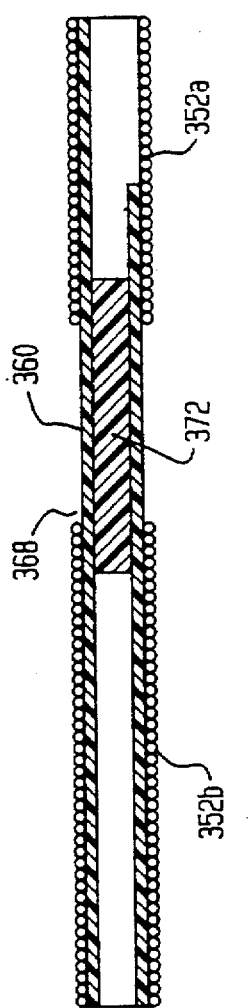
FIG. 35 is a cross sectional view taken along line E—E of FIG. 36 of the distal portion of a fourth version of a barb anchor insertion guide wire embodiment.
Figure 36:
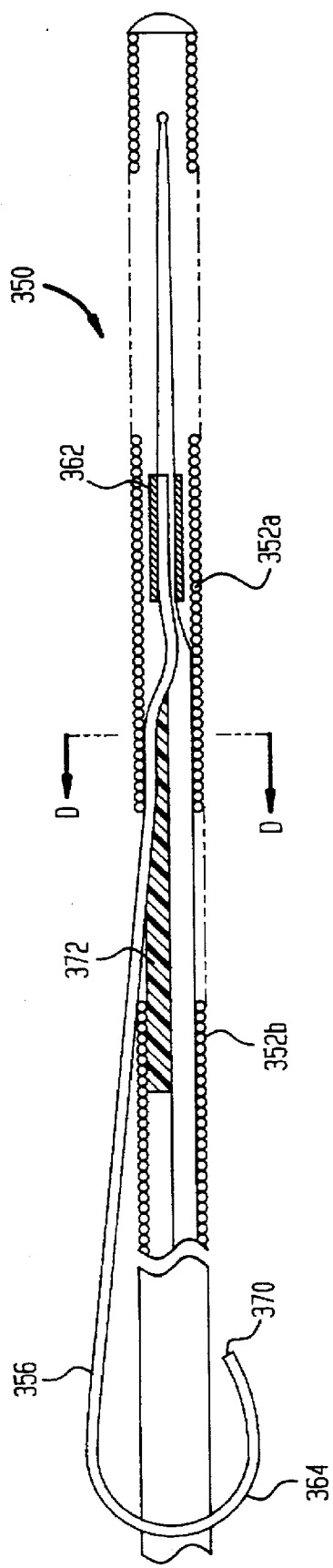
FIG. 36 is a cross sectional view taken along line D—D of FIG. 35.
Figure 37:
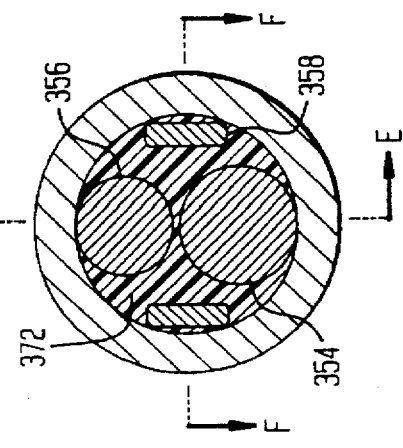
FIG. 37 is a cross sectional view taken along line F—F of FIG. 36 with the core wire removed.

A fourth version of the barb embodiment of the instant invention is depicted in FIGS. 35–37. This fourth version is identical to the version of FIGS. 32–34 except that in this fourth version the empty space in the notch area between core wire 354 and barb 356 is filled with a plastic compound 372. This plastic fill helps tip 370 find and exit through notch 368. Plastic fill 372 can also serve to support and hold sections 352a and 352b in position but apart from one another. Plastic fill 372 can serve this support function together with safety wires 358 and 360 or instead of one or both of those.

The third embodiment of this invention is depicted in FIGS. 38–43. In this embodiment, the anchor is formed by starting with a standard guide wire in which the outer sheath is formed of a wire coil. The distal end is turned back upon itself to form a loop of greater than 360°. Where the coil overlaps itself, the coils are spread apart and the adjacent coils interleaved. A core wire is used to lock those coils in that interleaved condition.

Figure 38:
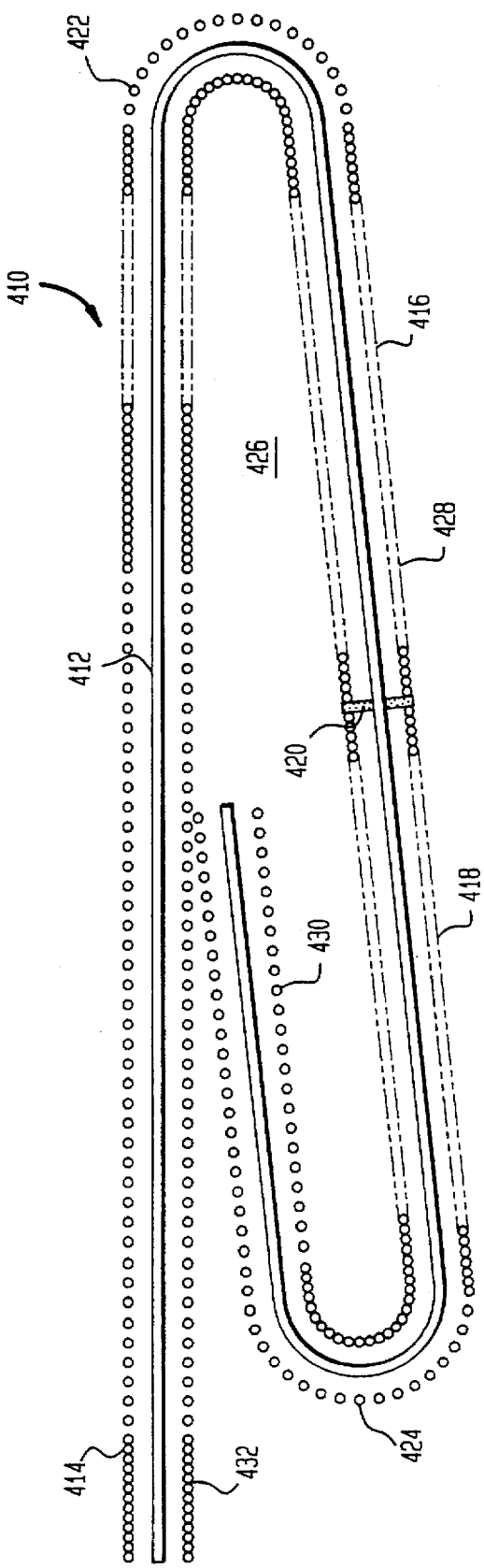
FIG. 38 is a cross sectional view of the distal portion of an interlocking coil loop anchor insertion guide wire according to the present invention in the process of being assembled.
Figure 39:
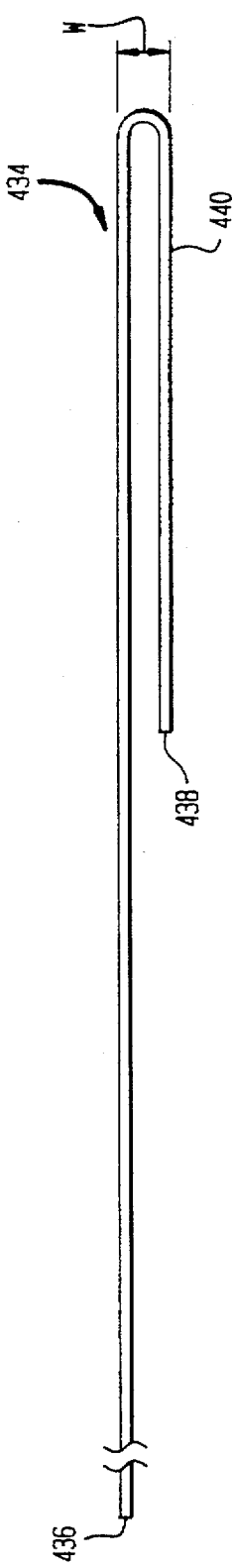
FIG. 39 is a plan view of a locking core wire for use in the insertion guide wire of FIG. 38.

FIG. 38 shows the distal portion of an insertion guide 410 wire according to this embodiment in the process of being assembled. Insertion wire 410 is a modified standard guide wire comprised of a safety wire 412 and a wire coil sheath 414. Sheath 414 is comprised of two sections of coil wire, a main section 416 and a reverse section 418. Coil sections 416 and 418 are wound with opposite hand pitch. For example, main coil 416 could be wound with a right hand pitch and reverse coil 418 with a left hand pitch or vice versa. Sections 416 and 418 are joined at 420 by conventional means, for example, by butt brazing and each is preferably brazed over a distance of about 1/16" back from junction 420.

Main coil 416 may be comprised of a biocompatible metal, for example stainless steel, and reverse coil 418 may be comprised of this same or a different biocompatible material, while safety wire 412 is preferably stainless steel.

The distal portion of insertion guide wire 410 is bent twice, once to form radius end 422 in main coil 416 and again to form opposite radius end 424 in reverse coil 418, thereby producing an elongated loop 426 having on overall arc of greater than 360°. In addition to having two radius ends, loop 426 has two parallel sides 428 and 430 with coils 416 and 418 being joined along parallel side 428. Parallel side 430, because loop 426 is greater than 360°, overlaps the main body of coil 416.

Running through lumen 432 of insertion guide wire 410 from proximal end 443 is locking core wire 434 which has a proximal tip 436 and a distal tip 438 and which is bent over at its distal end to form hook 440. The width W of hook 440 is sufficiently small so that it can slide easily within lumen 432.

At the proximal end of insertion guide wire 410, locking core wire 434 extends beyond the proximal end 442 of wire coil sheath 414, through split sleeve 444 into proximal coil 446. The proximal end 436 of core wire 434 is affixed, by any number of well known means, for example, by use of adhesives, crimping, brazing or shrink fitting, to proximal coil 446. Preferably, proximal coil 446 has the same inside and outside diameters as those of wire coil sheath 414. Proximal coil 446 is provided, at its proximal end, with a rounded tip 448.

In order to assemble the insertion guide wire, locking core wire 434 is inserted into lumen 432 of coil sheath 414 until tip 438 is distal of tip 462 of reverse coil 418. The coils of side 430 are then spread apart as are the coils of main section 416 which are adjacent side 430. The adjacent spread coils are then pushed together so that they interleave and locking core wire 434 is slid proximally so that hook 440 enters into the space between the interleaved coils. The interleaved coils can then be released since hook 440 is holding them in their interleaved condition. By holding the adjacent coils interleaved, hook 440 maintains loop 426 in the distal end of insertion guide wire 410.

Insertion and use of this embodiment is substantially as described above with respect to the first embodiment.

As noted earlier, insertion wire 410 is comprised of a locking core wire 434, wire coil sheath 414, split sleeve 444 and proximal coil 446. Sheath 414 has a lumen 432 within which locking core wire 434 is slidable. Since the proximal end of core wire 434, i.e., the end which is proximal of split sleeve 444, is affixed to coil 446, core wire 434 can be made to slide axially within sheath 414 by pushing on coil 446 while holding the medial portion of sheath 414.

Absent the application of axial force in the distal direction, split sleeve 444 prevents core wire 434 from inadvertent distal movement within wire coil sheath 414. When a physician applies distally directed force on proximal coil 446, initially, split sleeve 444 resists such forward movement of proximal coil 446. However, continued force applied to coil 446 causes split sleeve 444 to buckle and separate along its slit thereby permitting core wire 434 to move distally within core wire sheath 414.

After the guide sheath has been withdrawn to a point just proximal to the proximal end of the collagen plug, as described above, tension T is released and insertion wire 410 is advanced slightly further into the artery, perhaps an additional 1–2 inches. Then, while wire sheath 414 is held in one hand, proximal coil 446 is pushed distally in the direction of arrow R" (FIG. 41) relative to sheath 414 until tip 438 at the end of hook 440 passes out of between the interleaved coils. Those coils, once no longer restrained by hook 440, separate and loop 426 opens. The insertion wire 410 is then pulled in a proximal direction. As the region of junction 450 reaches the arterial puncture, the unrestrained coils easily straighten out and guide wire 410 can exit without impediment.

While the subject matter of this invention has been described in connection with several specific embodiments, it should be understood that numerous modifications could be made by persons of skill in this art without departing from the inventive concept described herein. Accordingly, the above description is intended to be merely illustrative and not limiting. The scope of the invention claimed should be understood as including all those alternatives, variants, modifications and equivalents which the above specification would readily suggest or which would readily occur or be apparent to one skilled in the art upon reading the above.

What is claimed is:

1. A method for inserting hemostatic material into a wound in a patient wherein said wound is comprised of a puncture in the patient's skin, a puncture in one of the patient's arteries and a wound channel between said punctures, said method comprising the steps of inserting into said wound a guide wire having a proximal end, a distal end, a medial portion and a longitudinal axis, said distal end having been formed into an anchor, said insertion continuing until said anchor has passed through said arterial puncture and said proximal end is outside the patient's body, pulling back on said guide wire until said anchor catches on the inside of said artery, inserting said hemostatic material over said guide wire and along said medial portion thereof until said hemostatic material is in said wound channel adjacent said arterial puncture, and releasing said anchor and removing said guide wire from said wound.

2. The method as claimed in claim 1, further comprising the steps of inserting a sheath and a dilator over said guide wire and removing said dilator before inserting said hemostatic material through said sheath.

3. The method as claimed in claim 2, wherein said hemostatic material is housed in a preloaded canister and is inserted into said wound channel through said sheath.

4. The method as claimed in claim 2, wherein locating means are provided for determining when said sheath is properly located in said wound channel with respect to said arterial puncture, said method further comprising the step of inserting said sheath until said locating means indicates that said sheath is located at a predetermined position relative to said arterial puncture.

5. A method for inserting hemostatic material into a wound in a patient wherein said wound is comprised of a puncture in the patient's skin, a puncture in one of the patient's arteries and a wound channel between said punctures and wherein a procedural sheath is in situ with its distal tip inside said artery and its proximal end outside of the patient, said method comprising the steps of inserting a guide wire into said procedural sheath, said guide wire having a proximal end, a distal end, a medial portion and a longitudinal axis, said distal end having been formed into an anchor, said insertion continuing until said anchor has emerged from the distal end of said procedural sheath, removing said procedural sheath from the patient, pulling back on said guide wire until said anchor catches on the inside of said artery, inserting said hemostatic material over said guide wire and along said medial portion thereof until said hemostatic material is in said wound channel adjacent said arterial puncture and, releasing said anchor and removing said guide wire from said wound.

6. The method as claimed in claim 5, further comprising the step of using a funnel to insert said anchor into said procedural sheath.

7. The method as claimed in claim 5, further comprising the step of inserting a guide sheath over said guide wire after said removal of said procedural sheath.

8. The method as claimed in claim 7, wherein said hemostatic material is inserted through said guide sheath.

9. The method as claimed in claim 8, wherein said hemostatic material is housed in a preloaded canister, said method further comprising the step of forcing said hemostatic material from said canister into said guide sheath.

10. An insertion guide wire having a distal end and a proximal end, comprising:

a sheath having a proximal end, a distal end and a lumen therein, said distal end of said sheath being comprised of a wire coil and being formed into a loop having a total arc of greater than 360° so that said wire coil overlaps upon itself in an overlapping portion, at least some of said coils in said overlapping portion being interleaved; and a core wire in said lumen, said core wire having a proximal end and a distal end, said distal end of said core wire being bent back upon itself to form a hook, said hook retaining said overlapping coils in said interleaved condition.

11. An insertion guide wire according to claim 10, wherein said core wire is slidable within said lumen.

12. An insertion guide wire according to claim 10, further comprising means for moving said core wire axially within said lumen.

13. An insertion guide wire according to claim 12, wherein said core wire is slidable toward said distal end of said sheath so as to release said overlapping coils from said interleaved condition thereby to enable said loop to straighten out.

14. An insertion guide wire according to claim 12, wherein said core wire moving means enables control of said axial movement of said core wire from said proximal end of said insertion guide wire.

15. An insertion guide wire according to claim 12 wherein said wire coil is comprised of two adjoined coils of opposite hand thread and wherein said overlapping coils are of opposite hand thread.

16. An insertion guide wire according to claim 10, further comprising a safety wire.

17. An insertion guide wire according to claim 12, further comprising means for temporarily resisting axial movement in the distal direction of said core wire.

18. An insertion guide wire according to claim 17, wherein said resisting means is comprised of a split sleeve.

19. A guide wire, comprising a sheath having a longitudinal axis, a proximal end, a distal end and a lumen extending from said proximal end toward said distal end;

an aperture formed in an intermediate portion of said sheath at a spaced distance from said distal end, said aperture delimiting a distal portion of said sheath between said distal end and said aperture;

a core wire slideably arranged in said sheath and having a proximal end and a distal end, said core wire being movable between a first position in which an intermediate portion of said core wire between said proximal and distal ends protrudes from said sheath through said aperture and a second position in which said distal end of said core wire is positioned between said proximal end of said sheath and said aperture;

said distal portion of said sheath being held between said intermediate portion of said sheath and said intermediate portion of said core wire with said core wire in said first position to define an anchor having a component projecting in a direction transverse to said longitudinal axis, whereby movement of said core wire from said first position to said second position releases said anchor.

20. A guide wire as claimed in claim 19, wherein said anchor includes a bended region in said guide wire, said guide wire having a greater degree of bendability in said bended region than in a region proximal of said bended region.

21. A guide wire as claimed in claim 20, wherein said core wire extends through said sheath in said bended region, and said greater degree of bendability is achieved by providing said core wire with a reduced diameter in said bended region.

22. A guide wire as claimed in claim 21, further comprising a wire spring wrapped around said reduced diameter of said core wire.

23. A guide wire as claimed in claim 20, wherein said core wire includes a proximal portion and a distal portion separated by a space, said space being located in said bended region.

24. A guide wire as claimed in claim 20, further comprising a cannula arranged around a portion of said core wire distally of said bended region.

25. A guide wire as claimed in claim 24, wherein said distal end of said sheath is separated from a remaining portion of said sheath by a predetermined distance, said distal end and said remaining portion being joined together by said cannula.

26. A guide wire as claimed in claim 19, wherein said anchor is in the form of a loop defining an arc of at least 360°, one portion of said loop being positioned on one side of said longitudinal axis and another portion of said loop being positioned on another side of said longitudinal axis.

27. A guide wire as claimed in claim 19, wherein said intermediate portion of said core wire forms an angle of less than about 180° with said longitudinal axis.

28. A guide wire as claimed in claim 19, further comprising locating means for indicating a predetermined distance from said aperture.

29. A system for stanching the flow of blood from an internal wound wherein there is communication between the internal wound and the external world through a wound channel and a skin puncture, said system comprising a guide wire including a sheath having a longitudinal axis, a proximal end, a distal end and a lumen extending from said proximal end toward said distal end, an aperture formed in an intermediate portion of said sheath at a spaced distance from said distal end, said aperture delimiting a distal portion of said sheath between said distal end and said aperture, and a core wire slideably arranged in said sheath and having a proximal end and a distal end, said core wire being movable between a first position in which an intermediate portion of said core wire between said proximal and distal ends protrudes from said sheath through said aperture and a second position in which said distal end of said core wire is positioned between said proximal end of said sheath and said aperture, said distal portion of said sheath being held between said intermediate portion of said sheath and said intermediate portion of said core wire with said core wire in said first position to define an anchor having a component projecting in a direction transverse to said longitudinal axis, whereby movement of said core wire from said first position to said second position releases said anchor;

a plug of hemostatic material sized to pass through the wound channel, said plug having a through lumen for slideably receiving said guide wire; and means for advancing said hemostatic material through the wound channel to the internal wound.

30. A system as claimed in claim 29, further comprising a placement sheath sized for insertion in the wound channel and having a lumen for receiving and advancing said plug of hemostatic material through the wound channel.

31. A system as claimed in claim 29, further comprising means for indicating when said plug of hemostatic material is positioned adjacent the internal wound.

32. A system as claimed in claim 29, further comprising a funnel to facilitate insertion of said distal end of said guide wire into the wound channel.

33. A guide wire, comprising a sheath having a longitudinal axis, a proximal end, a distal end and a lumen extending from said proximal end toward said distal end;

an aperture formed in an intermediate portion of said sheath at a spaced distance from said distal end;

a core wire slideably arranged in said sheath and having a proximal end and a distal end; and a barb having one end attached to said core wire, another end and an intermediate portion between said one end and said another end;

said core wire being movable between a first position in which said intermediate portion of said barb protrudes from said sheath through said aperture and a second position in which said intermediate portion of said barb is positioned entirely within said lumen of said sheath.

34. A guide wire as claimed in claim 33, wherein said distal end of said sheath includes a flexible tip.

35. A guide wire as claimed in claim 33, wherein said distal end of said core wire includes a flexible tip.

36. A guide wire as claimed in claim 33, wherein said another end of said barb includes a J-tip.

37. A guide wire as claimed in claim 33, wherein said sheath is formed from a wire coil.

38. A guide wire as claimed in claim 33, wherein said sheath is formed from a biocompatible plastic.

39. A guide wire as claimed in claim 33, wherein said sheath includes a distal portion and a proximal portion separated by a predetermined distance, said aperture defining said predetermined distance.

40. A guide wire as claimed in claim 39, further comprising at least one safety wire for supporting said proximal and said distal portions of said sheath separated by said predetermined distance.

41. A guide wire as claimed in claim 39, further comprising an intervening plastic filler between said proximal and distal portions of said sheath.

42. A guide wire as claimed in claim 33, further comprising a safety wire assembled in said lumen of said sheath.

43. A guide wire as claimed in claim 33, further comprising means for temporarily resisting axial movement of said core wire in a direction toward said distal end of said sheath.

44. A guide wire as claimed in claim 43, wherein said resisting means includes a split sleeve assembled on said core wire between said proximal end of said core wire and said proximal end of said sheath.

* * * * *

UNITED STATES PATENT AND TRADEMARK OFFICE
CERTIFICATE OF CORRECTION

PATENT NO. : 5,728,122

DATED : March 17, 1998

INVENTOR(S) : Leschinsky, et al.

It is certified that error appears in the above-identified patent and that said Letters Patent is hereby corrected as shown below:

Column 7, line 46, "preformed" should read --pre-formed--.

Column 10, line 51, "core wire, 212" should read --core wire 212,--
and after "sheath" cancel ",".

Column 11, line 14, "core wire sheath, 214" should read --core wire sheath 214,--
and after "sleeve", cancel ",".

Column 16, line 10, after "claim 12" insert --,--.

Column 17, line 4, "are" should read --arc--.

Signed and Sealed this

Twenty-first Day of July, 1998

Attest:

BRUCE LEHMAN

Attesting Officer

Commissioner of Patents and Trademarks